United States Patent
Bunch et al.

(10) Patent No.: US 10,182,725 B2
(45) Date of Patent: Jan. 22, 2019

(54) ANATOMICAL VESSEL HEAT SENSORS

(71) Applicant: Intermountain Intellectual Asset Management, LLC, Salt Lake City, UT (US)

(72) Inventors: T. Jared Bunch, South Jordan, UT (US); Troy J. Orr, Draper, UT (US)

(73) Assignee: Intermountain Intellectual Asset Management, LLC, Salt Lake City, UT (US)

(*) Notice: Subject to any disclaimer, the term of this patent is extended or adjusted under 35 U.S.C. 154(b) by 64 days.

(21) Appl. No.: 13/763,696

(22) Filed: Feb. 10, 2013

(65) Prior Publication Data

US 2013/0211282 A1     Aug. 15, 2013

Related U.S. Application Data

(60) Provisional application No. 61/597,291, filed on Feb. 10, 2012.

(51) Int. Cl.
| | |
|---|---|
| *A61B 5/01* | (2006.01) |
| *A61B 18/02* | (2006.01) |
| *A61B 18/18* | (2006.01) |
| *A61B 18/12* | (2006.01) |
| *A61B 5/00* | (2006.01) |

(Continued)

(52) U.S. Cl.
CPC ............ *A61B 5/01* (2013.01); *A61B 5/6853* (2013.01); *A61B 18/02* (2013.01); *A61B 18/12* (2013.01); *A61B 18/1815* (2013.01); *A61B 5/4233* (2013.01); *A61B 5/4836* (2013.01); *A61B 5/687* (2013.01); *A61B 18/1492* (2013.01); *A61B 2018/00023* (2013.01); *A61B 2018/00041* (2013.01); *A61B 2018/00357* (2013.01); *A61B 2018/00577* (2013.01); *A61B 2018/00791* (2013.01); *A61B 2018/0212* (2013.01);

(Continued)

(58) Field of Classification Search
None
See application file for complete search history.

(56) References Cited

U.S. PATENT DOCUMENTS

| | | |
|---|---|---|
| 3,898,431 A | 8/1975 | House et al. |
| 6,053,912 A | 4/2000 | Panescu et al. |

(Continued)

FOREIGN PATENT DOCUMENTS

| | | | |
|---|---|---|---|
| WO | WO 2012068580 A1 * | 5/2012 | ............ A61B 18/02 |
| WO | WO2013/120042 | 8/2012 | |
| WO | WO2013/120043 | 8/2012 | |

OTHER PUBLICATIONS

"Resistance in a Conductor", www.regentsprep.org/Regents/physics/phys03/bresist/default.htm, Dec. 23, 2010.*

(Continued)

*Primary Examiner* — Matthew Kremer
(74) *Attorney, Agent, or Firm* — Stoel Rives LLP

(57) ABSTRACT

Heat sensors can be positioned within an anatomical vessel of a patient so as to monitor temperature changes, such as during ablation procedures in the heart. Some heat sensors can include a wire that defines an extended heat sensing region capable of detecting a change in the local temperature. Some heat sensors can be conformable to an inner surface of a wall of an anatomical vessel to maintain contact therewith or to be in close proximity thereto.

37 Claims, 32 Drawing Sheets

(51) Int. Cl.
*A61B 18/14* (2006.01)
*A61B 18/00* (2006.01)

(52) U.S. Cl.
CPC ............... *A61B 2018/1861* (2013.01); *A61B 2562/0271* (2013.01)

(56) References Cited

U.S. PATENT DOCUMENTS

| | | | |
|---|---|---|---|
| 6,135,976 A * | 10/2000 | Tachibana | A61K 41/0028 604/101.03 |
| 6,438,400 B1 | 8/2002 | Beard et al. | |
| 9,044,143 B2 | 6/2015 | Bunch et al. | |
| 2003/0009165 A1* | 1/2003 | Edwards et al. | 606/41 |
| 2003/0088299 A1 | 5/2003 | Magers et al. | |
| 2004/0147852 A1* | 7/2004 | Brister | A61B 5/015 600/549 |
| 2004/0260328 A1 | 12/2004 | Zvuloni et al. | |
| 2004/0267339 A1 | 12/2004 | Yon et al. | |
| 2004/0267739 A1 | 12/2004 | Dowling | |
| 2007/0049999 A1 | 3/2007 | Esch et al. | |
| 2007/0270793 A1 | 11/2007 | Lattouf | |
| 2009/0131930 A1* | 5/2009 | Gelbart et al. | 606/41 |
| 2010/0121159 A1* | 5/2010 | Burnett et al. | 600/301 |
| 2010/0179537 A1 | 7/2010 | Rashidi | |
| 2010/0204560 A1 | 8/2010 | Salahieh et al. | |
| 2010/0298895 A1* | 11/2010 | Ghaffari et al. | 607/3 |
| 2011/0264075 A1 | 10/2011 | Leung et al. | |
| 2012/0323089 A1 | 12/2012 | Feer et al. | |
| 2013/0030425 A1 | 1/2013 | Stewart et al. | |
| 2013/0211283 A1 | 8/2013 | Bunch et al. | |

OTHER PUBLICATIONS

"Temperature Dependence of Resistivy", www.tutorvista.com/content/physics/physics-iv/current-electricity/temperature-resistivity.php, Nov. 23, 2010.*

"Property Information: Resistivity", www-materials.eng.cam.ac.uk/mpsite/properties/non-lE/resistivity.html, Nov. 6, 2008.*

International Search Report and Written Opinion dated Feb. 10, 2013 for PCT/US2013/025471.

International Search Report and Written Opinion dated Feb. 10, 2013 for PCT/US2013/025472.

Preliminary Amendment dated Feb. 10, 2013 in U.S. Appl. No. 13/763,697.

Office Action dated Sep. 10, 2014 in U.S. Appl. No. 13/763,697.

Amendment dated Dec. 10, 2014 in U.S. Appl. No. 13/763,697.

Notice of Allowance and Notice of Allowability dated Jan. 21, 2015 in U.S. Appl. No. 13/763,697.

* cited by examiner

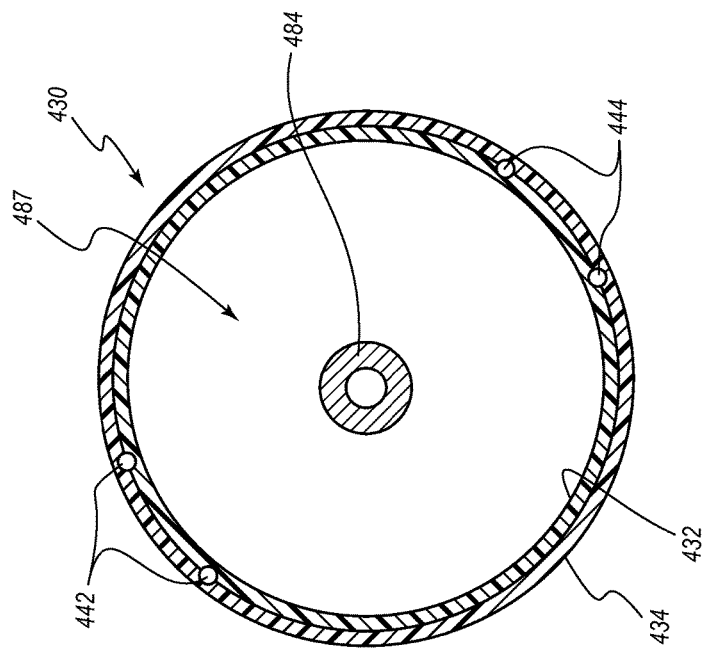
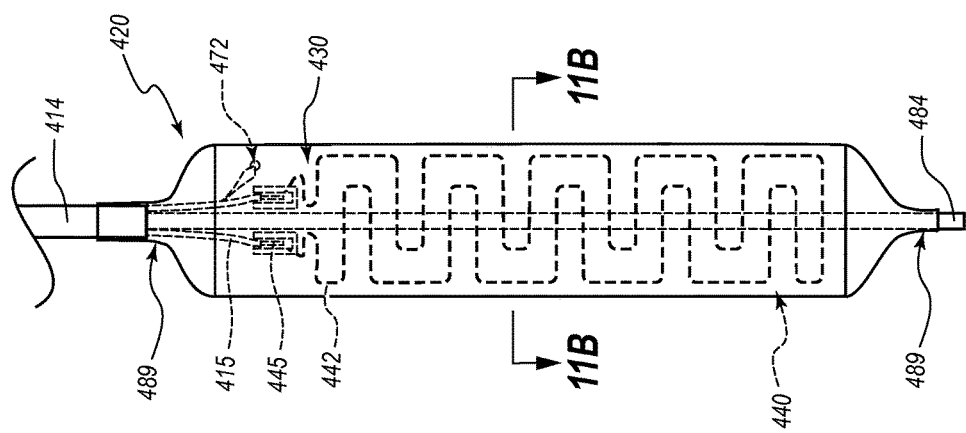
FIG. 11B
FIG. 11A

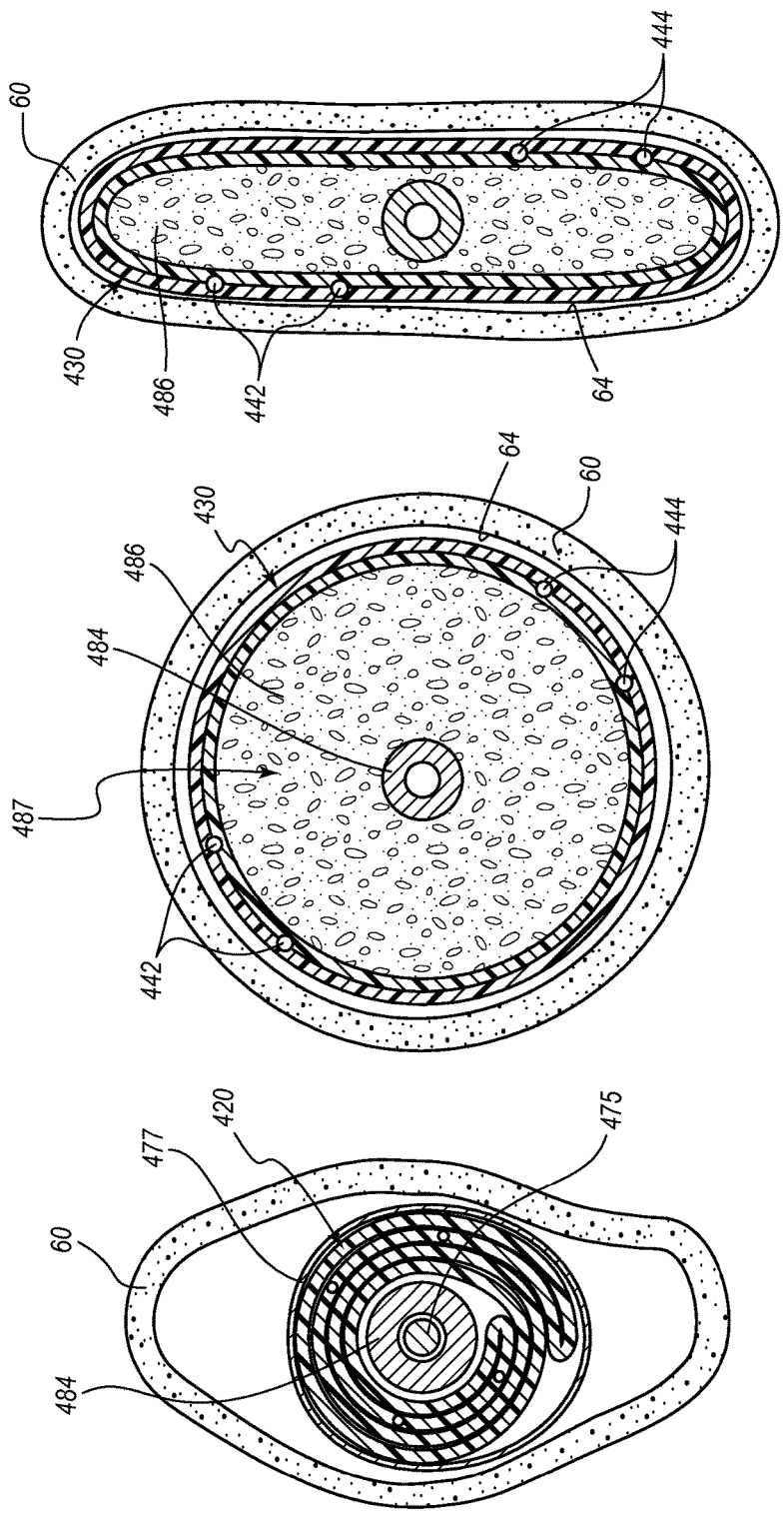

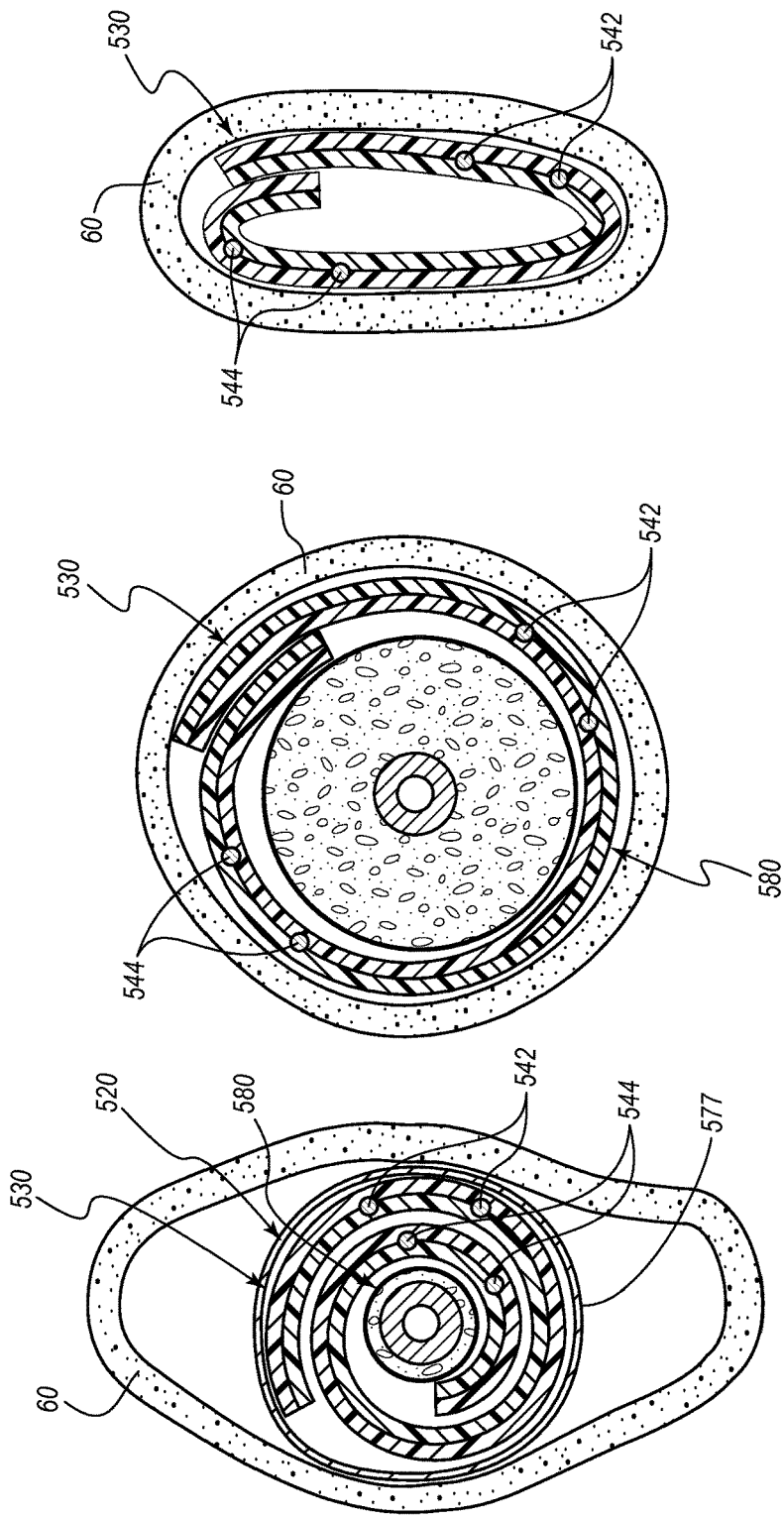

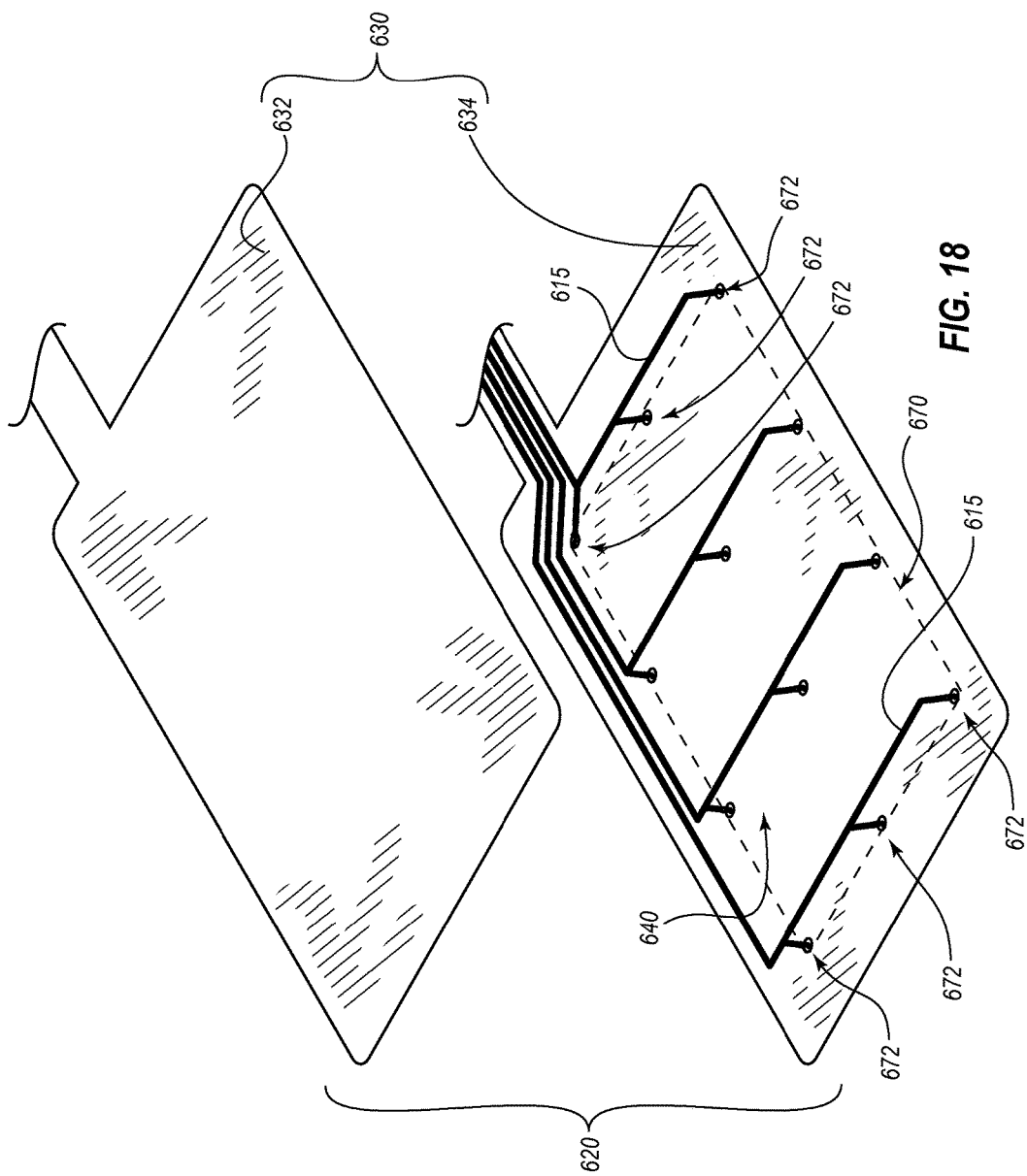

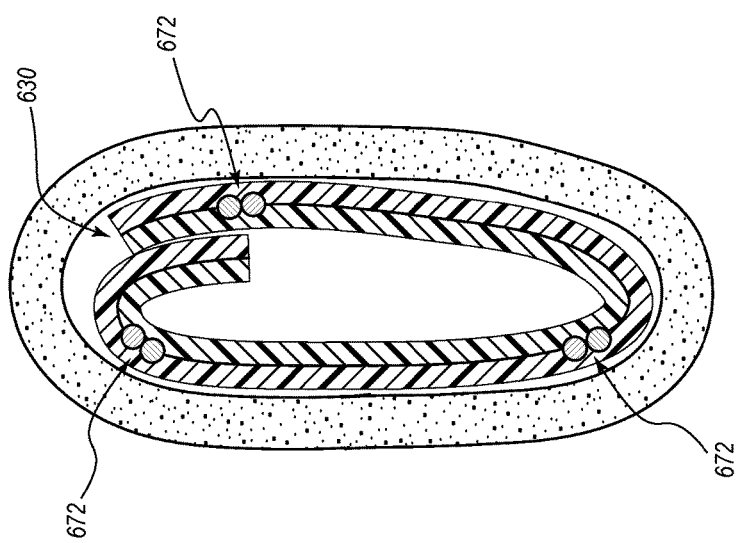
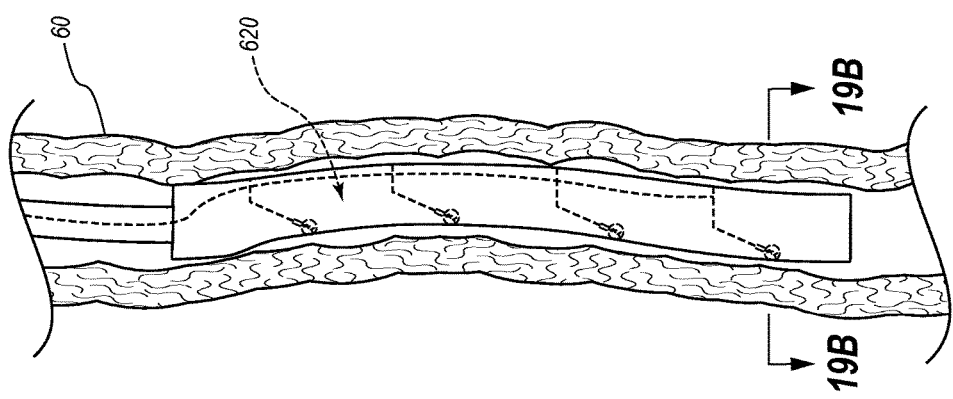
FIG. 19B
FIG. 19A

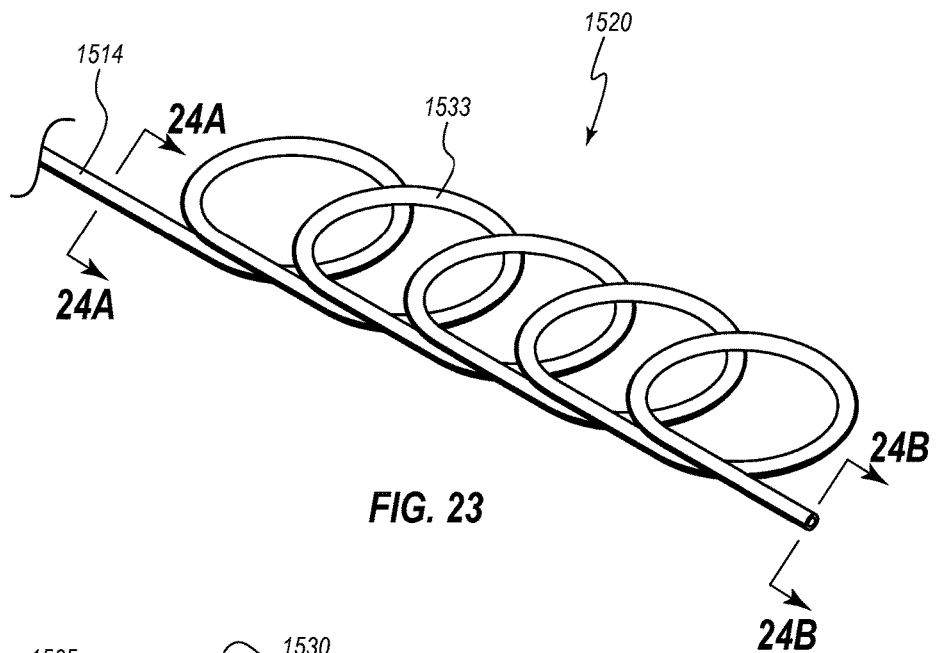
FIG. 23
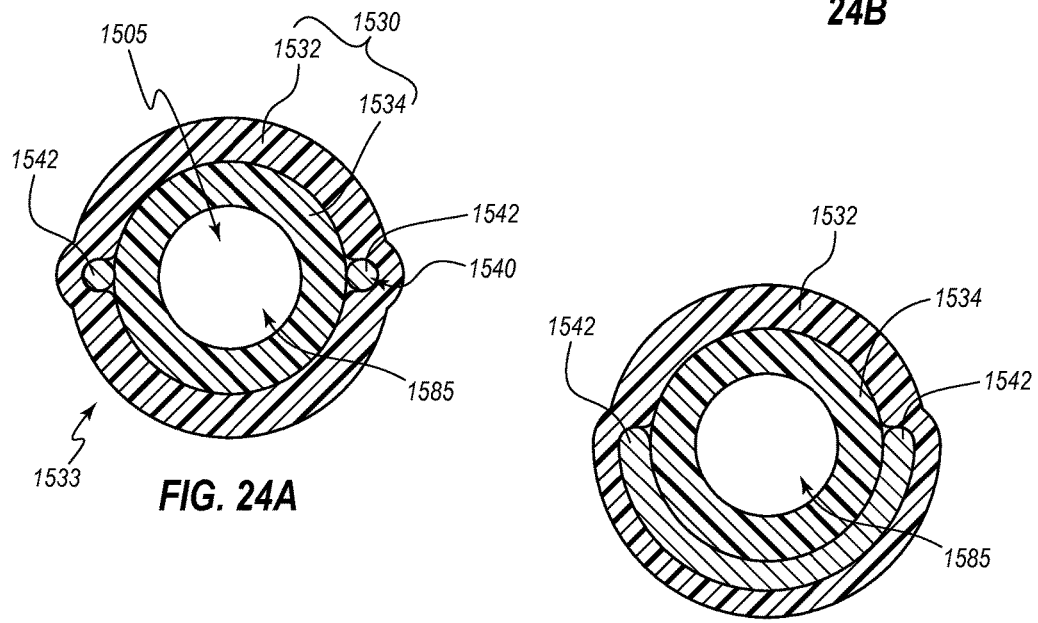
FIG. 24A
FIG. 24B

ANATOMICAL VESSEL HEAT SENSORS

CROSS-REFERENCE TO RELATED APPLICATIONS

This application claims the benefit under 35 U.S.C. § 119(e) of U.S. Provisional Patent Application No. 61/597,291, titled ESOPHAGEAL TEMPERATURE SENSOR, filed on Feb. 10, 2012, the entire contents of which are hereby incorporated by reference herein.

TECHNICAL FIELD

The present disclosure relates generally to medical heat sensors, and relates more particularly to heat sensors that can be deployed within the esophagus.

BRIEF DESCRIPTION OF THE DRAWINGS

The written disclosure herein describes illustrative embodiments that are non-limiting and non-exhaustive. Reference is made to certain of such illustrative embodiments that are depicted in the figures, in which:

FIG. 11A is an elevation view of another embodiment of a heat sensor compatible with the heat sensing system of FIG. 8A, wherein the heat sensor is shown prior to being packaged;

FIG. 11B is a cross-sectional view of the heat sensor of FIG. 11A taken along the view line 11B-11B;

FIG. 12A is a cross-sectional view of the heat sensor of FIG. 11A in a packaged state and positioned within the esophagus of a patient prior to deployment;

FIG. 12B is a cross-sectional view of the heat sensor of FIG. 11A in a deployed state, wherein the heat sensor has been expanded via an inflation fluid;

FIG. 12C is a cross-sectional view of the heat sensor of FIG. 11A in a compliance state in which the inflation fluid is at a lower pressure than that used to transition the heat sensor to the deployed state;

FIG. 17A is a cross-sectional view of the heat sensor of FIG. 14 in a packaged state and positioned within the esophagus of a patient prior to deployment;

FIG. 17B is a cross-sectional view of the heat sensor of FIG. 14 in a deployed state, wherein the heat sensor has been expanded via a balloon;

FIG. 17C is a cross-sectional view of the heat sensor of FIG. 14 in a compliance state in which the balloon has been removed;

FIG. 18 is an exploded perspective view of another embodiment of a heat sensor compatible with the heat sensing systems of FIGS. 1 and 8A;

FIG. 19A is a cross-sectional view of the heat sensor of FIG. 18 in a deployed state and in a compliance state that is positioned within the esophagus of a patient;

FIG. 19B is a cross-sectional view taken along the view line 19B-19B in FIG. 19A;

FIG. 23 is a perspective view of another embodiment of a heat sensor;

FIG. 24A is a cross-sectional view of the heat sensor of FIG. 23 taken along the view line 24A-24A in FIG. 23;

FIG. 24B is another cross-sectional view of the heat sensor of FIG. 23 taken along the view line 24B-24B in FIG. 23;

DETAILED DESCRIPTION

Figure 1:
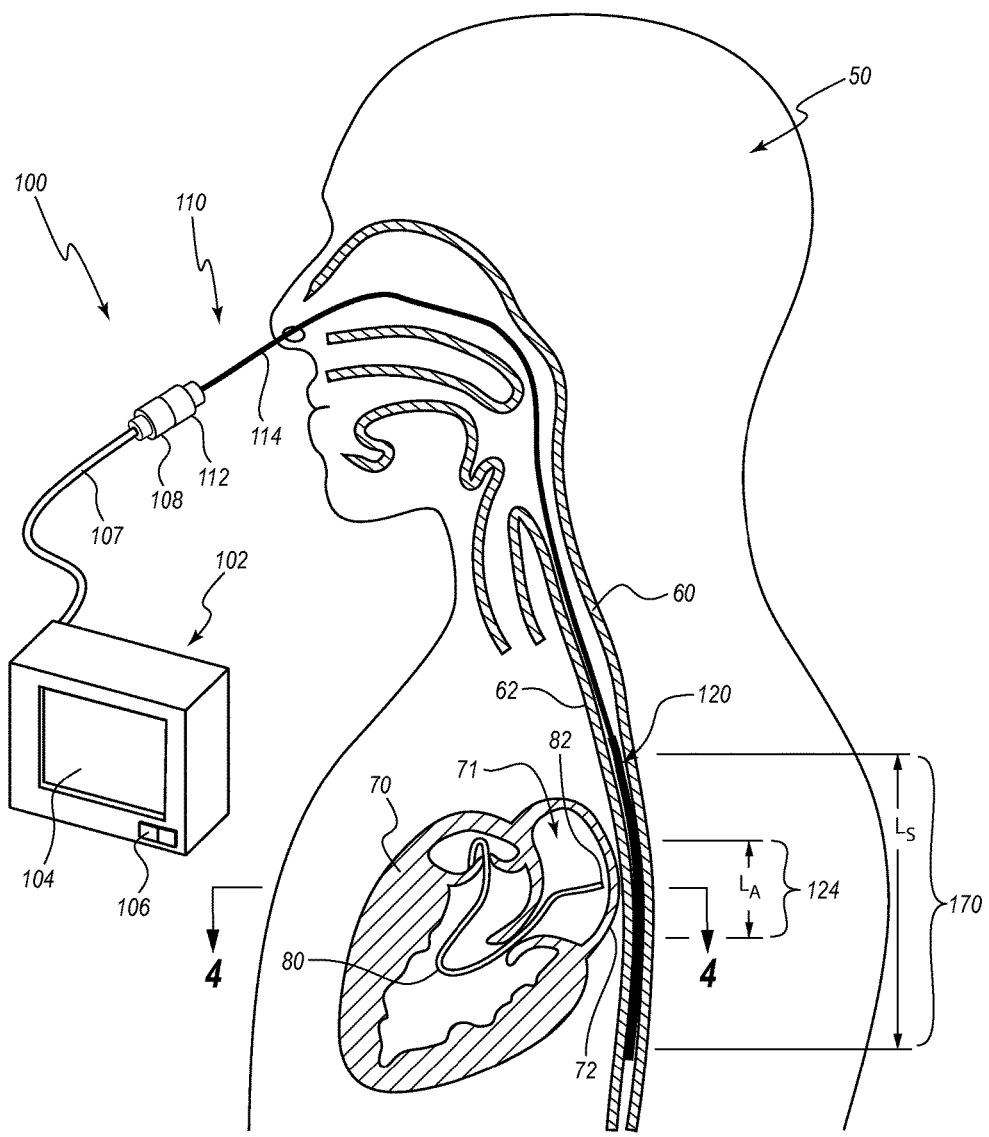
FIG. 1 is a perspective view of an embodiment of a heat sensing system, wherein an embodiment of a heat sensor is shown positioned within a patient that is schematically depicted in cross-section, and wherein the heat sensor is in use during a cardiac ablation procedure.

Atrial fibrillation ("AF") is a heart disease in which electrical impulses that are normally generated by the sinoatrial node are overwhelmed by disorganized electrical activity in the atrial tissue, leading to an irregular conduction of impulses to the ventricles that generate the heartbeat. The result is an irregular heartbeat, which may be intermittent or continuous. In human populations, AF-induced irregular heartbeat is a significant source of stroke, heart failure, disability, and death.

A number of surgical options are available for treating AF. One approach is widely known as the Cox-Maze III procedure. In this procedure, the left atrial appendage is excised, and a series of incisions and/or cryolesions are arranged in a maze-like pattern in the atria. The incisions encircle and isolate the pulmonary veins. The resulting scars block the abnormal electrical pathways, improving normal signal transmission and restoring regular heart rhythm. While its success rate is relatively good, the Cox-Maze III procedure and variations thereof are complex open-heart surgeries, that can require cardiopulmonary bypass, median sternotomy, and endocardial incisions that require suturing of the atria. The risks of complications from Cox-Maze III can be significant.

Some techniques use heating or cooling sources to create impulse-blocking lesions on the heart by ablation, rather than incision. Other ablation techniques have been developed that use one or more of incisions, cryoablation, microwave, and unipolar or bipolar radiofrequency ("RF") energy to create the pattern of lesions achieved in the original Cox-Maze III procedure. For example, certain unipolar RF techniques have been used for ablation in endocardial procedures. Endocardial ablation can result in perforation of surrounding organs, due mainly to the difficulty of achieving consistent burn penetration.

Some of the more serious complications that can arise from any of the foregoing ablation procedures are those caused by time-dependent, deep heating through excessive heat transfer. A perforation of the atrial wall due to excessive heating can cause permanent structural damage to the heart, or to the heart and to surrounding tissue. For example, excessive heat transmitted by RF energy or microwaves can permeate the thin wall of the left atrium and fuse it with the esophagus, forming a fistula between the two organs. This creates a pathway into the heart for bacteria from the esophagus, posing a significant risk of infection, endocarditis, systemic sepsis, and mediastinitis outside the heart and in the heart itself. Accordingly, it can be desirable to monitor the temperature of the esophagus wall, or stated otherwise, to detect changes to the temperature (e.g., heating or cooling), during certain ablation procedures. Such monitoring can assist in early detection of overheating (or, in the case of cryoablation, overcooling) of the atrial wall and/or the esophageal wall, which likewise can prevent or reduce damage to the heart and/or esophagus.

Disclosed herein are various embodiments of heat sensing systems and heat sensors that can be used during AF treatments so as to ameliorate or eliminate one or more of problems discussed above. In various embodiments, the heat sensors can be situated at a position within the esophagus that is nearest the tip of an ablation device, which tip may be at a position within the heart of the patient. Some heat sensors can have an extended region capable of detecting a rise (or, in the case of cryoablation, a fall) in the local temperature at any position within that region. In some embodiments, the heat sensors can be configured to conform to an inner surface of the esophageal wall so as to maintain contact therewith and/or so as to be in close proximity to the ablation device without altering the natural conformation of the esophagus. Such arrangements can permit monitoring of the temperature of the esophageal wall without substantially deforming the wall; for example, without moving the esophageal wall into closer proximity to the ablation site at the atrial wall. In other or further embodiments, the esophageal wall may be brought into proximity with (e.g., into contact with) the sensor after the sensor has been positioned within the esophagus at a desired location. In certain of such embodiments, the esophagus can be collapsed against the sensor, and may even be collapsed in a manner so as to provide additional spacing between the ablation tip and the esophagus. Other embodiments are also disclosed. The foregoing advantages and/or other advantages of various embodiments will be evident from the disclosure herein.

FIG. 1 is a perspective view of an embodiment of a heat sensing system 100 that can be used in any suitable medical procedure. In the illustrated embodiment, the heat sensing system 100 is configured for use during an AF ablation procedure. For example, a patient 50 can undergo any suitable ablation procedure of the left atrium wall 72 of the heart 70 of the patient. Any suitable ablation tool 80 can be introduced into the left atrium 71, and an ablation tip 82 can be positioned at or near the atrium wall 72. The ablation tip 82 can be used to create impulse-blocking lesions in the atrium wall 72 in any suitable manner, such as those described above. For example, in various embodiments, the tip 82 is configured to impart microwave and/or RF energy to the atrium wall 72 so as to heat specific regions of the wall, and/or to conduct cryoablation of the atrium wall 72 so as to cool specific regions of the wall. The ablation tool 80 may also be referred to as a heat source or, for cryoablation procedures, as a cooling source.

The wall 62 of the esophagus 60 of the patient can be in close proximity to the atrial wall 72 during the ablation procedure. Accordingly, in some instances, the procedure can heat and/or cool the esophageal wall 62. As previously discussed, it may be desirable to avoid significant temperature changes at the esophageal wall 62 so as to minimize or prevent tissue injury and/or perforation of the wall 62 and/or formation of a fistula between the esophagus 60 and the heart 70.

Accordingly, the heat sensing system 100 can be configured to monitor a temperature at the wall 62 of the esophagus 60 and/or to monitor changes in the temperature of the wall 62. In cases of microwave ablation or RF ablation, for example, the temperature of the wall 62 may increase, whereas in cases of cryoablation, the temperature may decrease. It should be appreciated that apparatus and methods disclosed herein with respect to the esophagus 60 and the ablation tool 80 that is used outside of the esophagus 60 may be used in other contexts. For example, various embodiments may be configured for use in other anatomical vessels, where heating (or cooling) occurs outside of the vessels or at the vessel walls. Moreover, various embodiments may be used with other mammalian esophagi and/or other anatomical vessels.

The heat sensing system 100 can include a monitor or controller 102, which may include one or more buttons or actuators 106 that are configured to effect one or more operations, such as navigating through menus, making selections, or otherwise providing commands. The controller 102 can include a display 104 that is configured to display information in a visually perceivable format. For example, the display 104 can comprise a screen of any suitable variety, including those presently known and those yet to be devised. For example, the screen 104 can comprise a liquid crystal display (LCD) panel. In some embodiments, the screen 104 can be configured to receive information or otherwise interact with a medical practitioner. For example, the screen 104 can comprise a touch screen. The controller 102 can be coupled with a heat sensing assembly 110, so as to communicate therewith, in any suitable manner. In the illustrated embodiment, the controller 102 and the heat sensing assembly 110 are coupled with each other via a cable 107 having a connector 108.

Various procedures discussed herein, such as monitoring of temperature, or detection of heating or cooling, can be accomplished via the monitor or controller 102. In some embodiments, the controller 102 can comprise a general-purpose or special-purpose computer, or some other electronic device, and at least a portion of the procedures may be embodied in machine-executable instructions therein. In other embodiments, at least a portion of the procedures (e.g., various steps or stages thereof) may be performed by hardware components that include specific logic for performing the steps or by a combination of hardware, software, and/or firmware.

The heat sensing assembly 110 can include a heat sensor 120 that is configured to be positioned within the esophagus 60 of the patient 50. The heat sensor 120 can be positioned at an end of a catheter 114, which may include electrical leads therein to permit communication between the controller 102 and the heat sensor 120. The catheter 114 may include a connector 112 that is configured to interface with the connector 108. The heat sensor 120 can be configured to detect a temperature and/or a change in temperature (e.g., heating or cooling). For example, in some embodiments, the heat sensor 120 comprises one or more electrically resistive elements that have temperature-dependent properties. In other embodiments, the heat sensor 120 comprises an array of thermocouples. Other suitable arrangements are also contemplated.

As shown in FIG. 1, in some embodiments, the heat sensor 120 may define a heat sensing zone or sensing region 170 that extends along a sensing length $L_S$. The sensing length $L_S$ may be significantly greater than a length $L_A$ of a temperature alteration zone or region 124. Having a heat sensing region 170 that exceeds a length of the temperature alteration zone 124 that may have an altered temperature (e.g., increased or decreased temperature) during an ablation procedure can aid in ensuring that the heat sensor 120 detects the temperature change, or stated otherwise, detects heating or cooling. Moreover, in some instances, the heat sensor 120 can be positioned within the esophagus 60 such that a portion of the length $L_S$ is distal to the position at which the ablation tip 82 is closest to the esophagus 60 and another portion of the length $L_S$ is proximal to the position at which the ablation tip 82 is closest to the esophagus 60, such as the position at which the atrial wall 72 is closest to the esophagus 60. In various embodiments, the length $L_A$ can be within a range of from about 2 centimeters to about 8 centimeters, and the length $L_S$ can be greater than the length $L_A$ and within a range of from about 4 centimeters to about 10 centimeters. In other or further embodiments, the length $L_S$ can be no less than about 2, 4, 6, 8, or 10 centimeters, no greater than about 4, 6, 8, or 10 centimeters, or within a range of from about 2 to 10, 4 to 10, or 4 to 8 centimeters. In some embodiments, the sensing length $L_S$ can be roughly the same length as a maximum length of the heart 70 of the patient 50. Other sensing lengths $L_S$ and temperature alteration lengths $L_A$ are also possible.

The temperature alteration zone 124 can extend through a volume of space at an interior of the esophagus 60. For example, in some embodiments, the temperature alteration zone 124 may be substantially conical, frustoconical, or cylindrical, depending on the manner in which heat propagates through an interior of the esophagus 60 due to a localized heat source at an exterior of the esophageal wall. In some instances, the temperature alteration zone 124 may be relatively small (although intense) near the position of the external heat source and may expand toward an opposing side of the esophageal wall. The length $L_A$ may also be referred to as a longitudinal length of the temperature alteration zone 124, as this length is measured in a direction corresponding to a longitudinal axis of the esophagus. The heat sensing region 170 can fully extend through the temperature alteration zone 124. For example, in the illustrated embodiment, and as discussed above, the heat sensor 120 is positioned such that a distal end thereof is distal to the temperature alteration zone 124 and such that a proximal end thereof is proximal to the temperature alteration zone 124.

Figure 2:
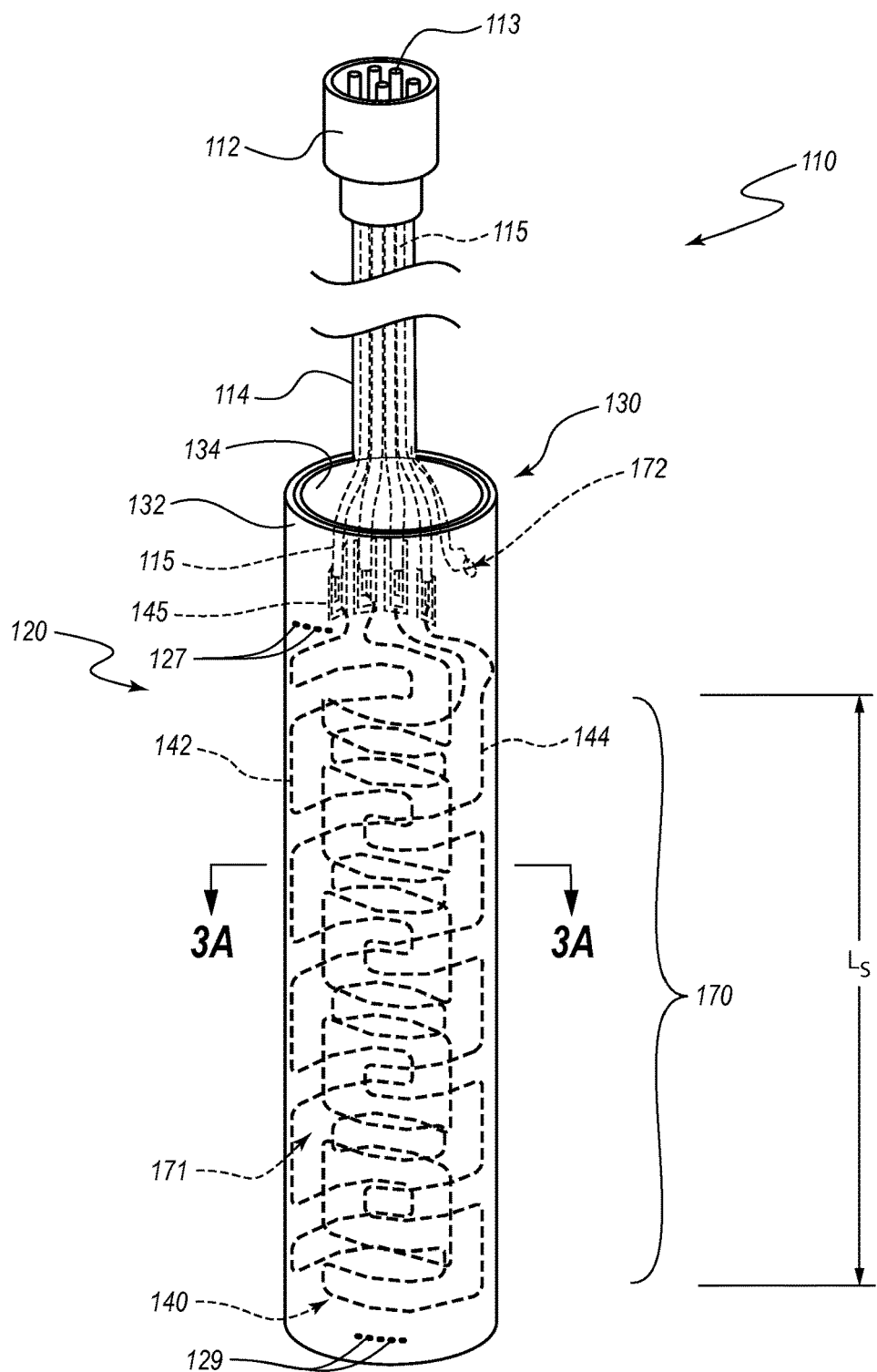
FIG. 2 is a partial perspective view of a heat sensing assembly portion of the heat sensing system of FIG. 1, which includes the heat sensor of FIG. 1.

FIG. 2 depicts the heat sensing assembly 110 in greater detail. In the illustrated embodiment, the connector 112 includes a plurality of electrical pins 113, each of which is coupled with an electrical lead 115 that extends through the cable or catheter 114 between the connector 112 and the heat sensor 120.

The heat sensor 120 can be configured to contact an inner surface of the esophagus 60, as further discussed below. The heat sensor 120 comprises a support structure 130 that can provide this contact in an electrically insulating manner and, in some embodiments, can support other components of the heat sensor 120. In the illustrated embodiment, the support structure 130 comprises a tube, sleeve, or sheath, although other arrangements are also possible, as discussed further below. Accordingly, the support structure 130 may also be referred to herein as a sheath for certain arrangements and/or as an electrically insulating structure. The terms support structure and electrically insulating structure are used synonymously herein. The illustrated sheath 130 comprises an outer layer 132, which may also be referred to as a cover or superstrate, and an inner layer 134, which may also be referred to as a base or substrate.

The heat sensor 120 can further include a heat sensing structure 140, which can be supported by the sheath 130. In the illustrated embodiment, the heat sensing structure 140 is sandwiched between and is enveloped or encapsulated by the inner and outer layers 134, 132 of the sheath 130. As further discussed below, the inner and outer layers 134, 132 of the sheath 130 may desirably comprise one or more electrically insulating or dielectric materials so as to electrically shield the heat sensing structure 140 from one or more electrically conductive substances, such as saliva, tissue, water, blood and/or other conductive materials within the esophagus 60.

Although the inner layer 134 constitutes the substrate and the outer layer 132 constitutes the superstrate in the illustrated embodiment, it should be appreciated that the orientation of the substrate and the superstrate can be reversed. For example, in some embodiments, the heat sensing structure 140 or other component is originally joined to the substrate in at least a temporary fashion, and then the superstrate is laminated, adhered, or otherwise attached to the substrate to encapsulate the heat sensing structure 140. However, other suitable techniques or methods may be used to encapsulate the heat sensing structure 140 between the substrate and the superstrate. Moreover, in the illustrated embodiment, the inner and outer layers 134, 132 are defined by separate pieces of material that are joined together. In other embodiments, the inner and outer layers 134, 132 (e.g., the substrate and the superstrate) can be formed of a unitary piece of material that is folded or otherwise formed in a manner that encapsulates the heat sensing structure 140.

The inner and/or outer layers 134, 132 can be formed of one or more materials that are not only insulating, but are also capable of conducting heat. For example, the support structure 130 can be configured to permit heat transfer to, from, or both to and from the heat sensing structure 140. In other or further embodiments, the inner and/or the outer layers 134 can comprise a biocompatible material that can contact portions of a patient's anatomy without adverse effects.

In the illustrated embodiment, the heat sensing structure 140 comprises two separate wires 142, 144, which may also be referred to as trace wires. Each wire 142, 144 has two ends, and each end is electrically coupled with a separate electrical lead 115 at a connection interface 145, which may also be referred to as a junction. In certain embodiments, the wires 142, 144 may be the same as or similar to those used in resistance thermometers, which are also known as resistance temperature detectors or resistive thermal devices (RTDs). In some embodiments, the wires 142, 144 extend over a greater area than standard RTDs, which often may be quite small and are used to measure a discrete temperature on a small area (e.g., no greater than about ¼ square inch) of a structure. The wires 142, 144 may comprise any suitable metallic or other material that exhibits desirable resistance properties. For example, in various embodiments, the wires 142, 144 can comprise platinum, copper, and/or nickel. The wires 142, 144 can have a unique, and repeatable and predictable resistance versus temperature (R vs. T) relationship and operating temperature range. The R vs. T relationship is defined as the amount of resistance change of the sensor per degree of temperature change. The predictable change in the resistance of the wires 142, 144 with a change in temperature can be used to detect and monitor heating from the ablation tool 80 within the esophagus 60, as further described below.

Platinum is a noble metal and has a more stable R vs. T relationship over a larger temperature range, as compared with nickel and copper. Nickel elements have a limited operational temperature range because the amount of change in resistance per degree of change in temperature becomes very non-linear at temperatures over 300° C. However, nickel can be suitable for temperature ranges experienced within the esophagus during various ablation procedures described herein. Copper also has a very linear resistance to temperature relationship, however, copper can oxidize at moderate temperatures and generally is not as well suited for temperatures over 150° C. Nevertheless, copper can also be suitable for certain temperature ranges experienced within the esophagus during various ablation procedures described herein.

Each of the wires 142, 144 can extend continuously in both a longitudinal direction (e.g., the direction of the central axis of the illustrated sensor 120) and in one or more lateral directions that are transverse to the longitudinal direction (e.g., perpendicular to or any other direction that is non-collinear with or nonparallel to the longitudinal direction). For example, in the illustrated embodiment, the wires 142, 144 have portions that extend in the longitudinal direction, which is a substantially vertical direction in the orientation shown in FIG. 2. The wires 142, 144 further extend about the perimeter or circumference of the illustrated sensor 120. Those portions of the wires 142, 144 that extend peripherally or circumferentially may be said to extend in two transverse directions that are perpendicular to the longitudinal direction. For example, if the longitudinal direction is defined as the Z-axis of the sensor 120, and if a plane that is perpendicular to the Z-axis includes perpendicular X- and Y-axes, then it may be said that the wires 142, 144 each extend in the Z-direction (longitudinally) and in both the X- and Y-directions (two lateral directions that are perpendicular to the longitudinal direction). Stated otherwise, the wires 142, 144 have various portions that include components in each of the X-, Y-, and Z-directions. The wires 142, 144 extend in multiple directions to define the heat sensing region 170. It may also be said that each wire 142, 144 is fixed to the substrate 134 in a circuitous path. The heat sensing region 170 thus extends over a finite area that is significantly greater than a single point. For example, thermocouples generally sense temperatures at a single point, which is at a junction of wires that comprise different materials. In contrast, the heat sensing region 170 defined by the heat sensing structure 140 can span an area that is much greater than the limited region that can be sensed by such thermocouples. In the illustrated embodiment, the heat sensing region 170 extends along the distance $L_S$ in the longitudinal direction. The heat sensing region 170 can further extend about a majority of a perimeter of the sheath 130. In various embodiments, the heat sensing region 170 can extend around no less than about ⅓, ½, ⅔, or ¾ of a perimeter of the sheath 130. In some embodiments, the heat sensing region 170 can extend about an entirety of the perimeter.

The heat sensor 120 can be sensitive to temperature changes that occur anywhere within the heat sensing region 170. For example, in some arrangements, if only a small portion of one of the wires 142, 144 is heated, the resistance of the heated portion will increase, such that the total resistance of the heated wire 142, 144 will likewise increase. In some instances, correlation between temperature and resistance of the wire 142, 144 can be used to determine the temperature at the heated portion of the wire 142, 144. However, in other instances, it may only be possible to determine that some amount of heating (or cooling) has occurred along at least a portion of the length of the wire 142, 144, although the temperature at that specific portion of the wire may not be determined and/or although the exact position along the wire 142, 144 at which the heating has occurred may not be determined. In some embodiments, it may be sufficient to determine that a temperature change of a sufficient magnitude has been effected anywhere within the heat sensing region 170 in order to conclude that damage to the esophagus 60 or other bodily structures may occur if ablation continues. Any suitable determination based on readings or measurements from the heat sensor 120 may be made by the controller 102. In view of functionalities of various embodiments of the heat sensor 120, the term "heat sensor" is sufficiently broad to include sensors and processes that detect a change in temperature, whether that change is an increase or a decrease (e.g., heating, as an increase in heat, or cooling, as a decrease in heat), even if the sensor does not determine what the temperature is at a given point and/or does not provide information from which the temperature can be determined. For example, the term "heat sensor" can include a "temperature change sensor," which is a sensor that is capable of detecting a change in temperature (e.g., due to heating or cooling) anywhere within a sensing region of the sensor. The sensor may be capable of detecting such a temperature change, even where the change occurs at only a portion of the sensing region. Similarly, the term "heat sensing" is sufficiently broad to include "temperature change sensing," in which changes in temperature (e.g., heating or cooling) are detected, even if an exact or specific temperature is not determined.

In some embodiments, multiple wires may be used and arranged in any suitable pattern so as to determine the position at which temperature has changed, as discussed below. However, in some embodiments, the actual position at which heating (or cooling) occurs within the esophagus 60 may not be important, so long as the heat sensor 120 is positioned to sense any temperature change due to an ablation procedure. That is, so long as any temperature change or heating due to the ablation procedure can be determined and monitored by any portion of the sensor 120, the temperature, or temperature change, information obtained by the heat sensor 120 may be sufficient. Such information can be used, for example, to conclude that the ablation procedure should be at least temporarily delayed or halted so as to prevent undesired damage to the esophagus 60 and/or other anatomical structures.

The illustrated embodiment can allow for a rough determination of whether one or both semi-cylindrical halves of the sensor 120 are undergoing temperature changes. Each of the two wires 142, 144 defines a substantially zigzag or serpentine pattern that doubles back on itself. Each wire 142, 144 is confined to one side (e.g., opposing 180-degree swaths) of a substantially cylindrically shaped sheath 130. It may be said that the wires 142, 144 define an array, grid, pattern, mesh, or lattice, which provides for a sensitive heat sensing region 170. Other arrangements of the wires 142, 144 are also possible. The array can be configured to provide information regarding a specific region of the heat sensing structure 140. For example, given the particular arrangement of the wires 142, 144 shown in FIG. 2, the resistance of one wire 142, 144 can be compared with that of the other wire 142, 144 so as to determine the differences in heating (or cooling) at one side of the sheath 130 relative to the other side of the sheath 130. In other or further embodiments, multiple wires may be positioned at different longitudinal positions, such that information may be obtained as to the longitudinal position of the sensor 120 at which heating takes place.

In other embodiments, the heat sensing structure 140 may comprise a single wire. In still further embodiments, the heat sensing structure 140 may comprise two or more, three or more, or four or more wires. The wire or wires may be arranged in any suitable configuration so as to define a relatively large heat sensing region 170. The plurality of wires may also be arranged as desired in any number of longitudinal positions and/or radial positions to permit provide information regarding the specific region or regions of the sensor 120 at which temperature changes occur. In some embodiments, the wire or wires may also have large openings or spaces 171 between adjacent branches thereof, such that a width of each space 171 is many times (e.g., 10, 100, or 1,000 or more times) greater than a diameter of the wire. Likewise, a surface area of the heat sensing region 170 can be much larger than the surface area of one or more electrical wires that define the heat sensing region 170. For example, in various embodiments, a full exterior surface of the one or more electrical wires can define a first surface area and an outermost boundary of the heat sensing region 170 can define a second surface area. In FIG. 2, the first surface area is defined as the total surface area of the wires 142, 144, and the second surface area is defined as the surface area of the cylindrical region that extends from the top end of the wires 142, 144 to the bottom end of the wires 142, 144 when the heat sensor 120 is in the depicted orientation. In various embodiments, the second surface area defined by the heat sensing region 170 can be no less than 50, 100, 500, or 1000 times the first surface area defined by the wires 142, 144. The large openings or spaces may permit the heat sensing structure 140 to be more compliant, as compared with more compactly spaced wires. However, in other embodiments, the wires may be more tightly compacted, but may be relatively flexible. In either case, the sensing structure 140 may be configured to yield to natural movements of the esophagus 60.

In some embodiments, the heat sensor 120 comprises a temperature sensor 172. Any suitable temperature sensor may be used, such as, for example, a thermocouple. Accordingly, the temperature sensor 172 may also be referred to as a thermocouple 172 in reference to the specific embodiment depicted in FIG. 2. The thermocouple 172 can be positioned near a proximal end of the support structure 130, and may be distanced from the heat sensing region 170. The thermocouple 172 can be used to obtain a temperature reading of a region of the esophagus 60 that is not expected to undergo temperature changes due to the ablation procedure. Stated otherwise, the thermocouple 172 can be positioned outside of the heat sensing region 170 to determine a representative temperature of the substrate 132 to which it is attached. Although outside of the heat sensing region 170, the thermocouple 172 may nevertheless be in close proximity to the region 170. In other embodiments, the thermocouple 172 may be positioned at an interior of the heat sensing region 170, and thus may also be in close proximity to the heat sensing region 170 in this manner. The thermocouple 172 can provide a baseline reading of temperature in the vicinity of the heat sensing region 170. The baseline may be used to calibrate the heat sensing region 140 in any suitable manner. The thermocouple 172 may also be referred to herein as a reference temperature sensor or as a baseline temperature sensor. The resistive element heat sensor 120 may be monitored in relation to the reference thermocouple 172. For example, in some arrangements, if the resistive element (e.g., one or more of the wires 142, 144) changes in electrical resistivity and the reference thermocouple 172 remains stable (e.g., does not change or changes by a relatively small amount), it may be concluded that the heat sensor 120 is detecting localized heating within the heat sensing region 170 (e.g., at a position along the sensing length $L_S$). In other embodiments, any suitable temperature sensor other than a thermocouple 172 may be used to determine reference temperature outside of the heat sensing region 170. In other or further embodiments, multiple reference temperature sensors, such as the reference thermocouple 172, may be positioned outside of the heat sensing region 170.

In certain embodiments, the heat sensor 120 includes one or more imaging markers 127, 129 for visualization of the heat sensor 120 during placement and/or use via fluoroscopy or any other suitable imaging technique. In the illustrated embodiment, an imaging marker 127 is placed at the proximal end of the heat sensor 120 and another imaging marker 129 is placed at the distal end of the heat sensor 120. Other arrangements and placements of the one or more imaging markers 127, 129 is also possible. Each marker 127, 129 may comprise any suitable substance, such as, for example, silver, gold, bismuth, cesium, thorium, tin, zirconium, tantalum, tungsten, and/or lanthanum and/or compounds thereof. In some embodiments, the markers 127, 129 may be referred to as radiopaque markers. The same or similar makers may be used with any of the heat sensors disclosed herein.

Figure 3B:
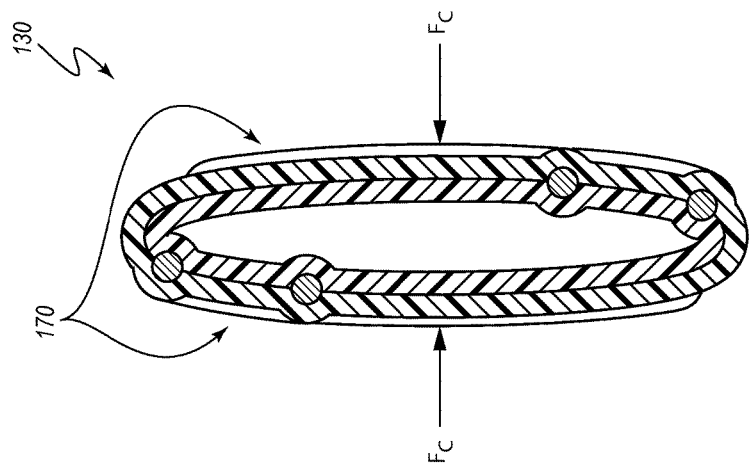
FIG. 3B is another cross-sectional view of the heat sensor of FIG. 1, similar to that shown in FIG. 3A, wherein the heat sensor is shown in a displaced or compressed state, which may also be referred to as a compliance state.
Figure 3A:
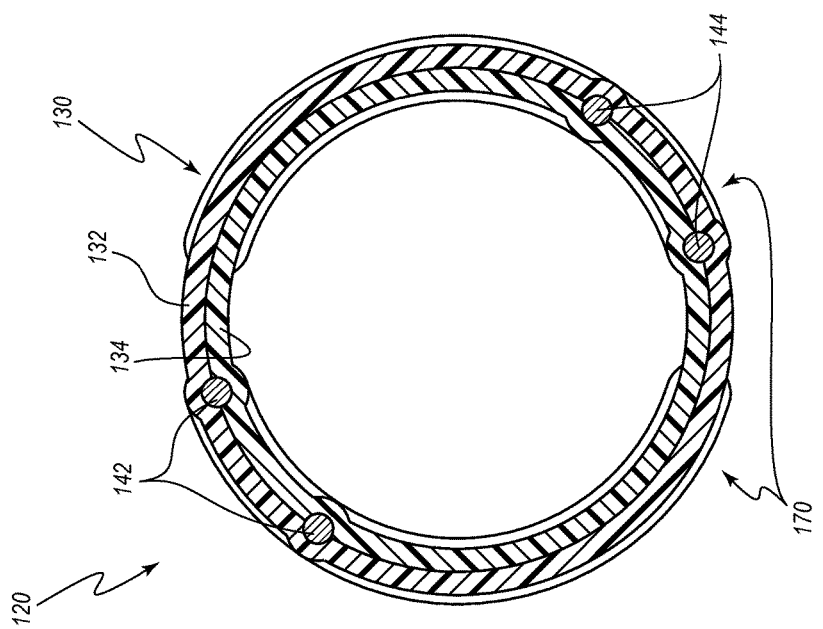
FIG. 3A is a cross-sectional view of the heat sensor of FIG. 1 taken along the view line 3A-3A in FIG. 2, wherein the heat sensor is shown in a natural or uncompressed state.

With reference to FIGS. 3A and 3B, the heat sensor 120 can be configured to transition between a natural or uncompressed state (FIG. 3A) and a displaced or compressed state (FIG. 3B), which may also be referred to as a compliance state. In the illustrated embodiment, the support structure 130 comprises an elastically resilient and flexible material that is biased toward the orientation shown in FIG. 3A, and the support structure 130 can be displaced or deformed to other orientations, such as that shown in FIG. 3B, upon application of forces thereto (e.g., the compression forces $F_C$). Upon removal or discontinuance of the displacement or deforming forces, the support structure 130 can return to its uncompressed state. In certain embodiments, the biasing forces that arise within the support structure 130 when deformed are relatively small in comparison to the forces applied by the esophagus 60, such that the support structure 130 is very compliant with respect to the esophagus 60. Accordingly, in some embodiments, the bias is sufficient to maintain the support structure 130 in an expanded state so as to contact and/or be in close proximity to an inner wall of the esophagus 60 without deforming the esophagus 60, or without substantially deforming the esophagus 60. For example, the support structure 130 can be sufficiently compliant to permit the esophagus 60 to be in a substantially relaxed or collapsed state, and will not expand the esophagus 60 into closer proximity to the atrial wall 72 of the heart 70, yet the support structure tracks, follows, conforms to, complies with, or accords with an inner surface of the esophagus 60. Such an arrangement is depicted in FIGS. 3B-5, as discussed further below, and may be referred to as a compliance state or as a tracking, following, conformance, or according state. As used herein, the term "without substantially deforming" includes situations in which no deformation takes place, but also includes situations in which negligible deformation takes place. For example, the support structure 130 may press against an inner surface of the esophagus 60 and may slightly compress the esophageal wall and/or may slightly displace or deform the esophageal wall. However, such deformations will not be significant, and may only move the esophageal wall marginally closer to the ablation site. In some instances, "substantial deformation" can be defined as increasing or decreasing one or more of the maximum transverse width (e.g., maximum diameter) and the minimum transverse width (e.g., minimum diameter) of the esophagus by an amount greater than 20 percent of the original magnitude thereof.

In the illustrated embodiment, the support structure 130 comprises a tube or sheath, which may be substantially cylindrical when in the uncompressed state, as shown in FIG. 3A. When positioned within the esophagus 60, the support structure 130 may be compressed into an oblong or ovoid configuration, such as that depicted in FIGS. 3B-5. If the esophagus 60 expands or becomes more cylindrical under normal or natural conditions, or upon other removal of the compressive forces $F_C$ (such as removal of the heat sensor 120 from the esophagus 60), the support structure 130 can move toward or return to the uncompressed configuration. The support structure 130 thus may be configured to maintain contact with, or otherwise maintain close proximity to, the inner surface of the esophagus 60. Maintaining contact or close proximity between the support structure 130 and the inner wall of the esophagus 60 can permit effective thermal transfer from the esophageal wall to the heat sensor 120 (e.g., particularly to the heat sensing resistive wires 142, 144). The esophagus 60 is depicted in a flattened cylindrical state, but any natural state of the esophagus is contemplated, including, for example, highly convex and/or convolute orientations.

As previously discussed, the support structure 130 may be flexible, malleable, or readily conformable so as to be displaced, compressed, transformed, altered, or reshaped into an orientation that tracks, follows, conforms to, complies with, or accords with an inner surface of the esophagus 60. Moreover, in the illustrated embodiment, the support structure 130 is resiliently flexible and is biased toward a natural configuration (e.g., a cylinder) that provides a degree of structural rigidity to the support structure 130. However, in other embodiments, the support structure 130 may not be biased toward a natural shape, and may instead be even more compliant, or stated otherwise, may be flaccid, limp, or slack. Certain of such embodiments may be pressed toward or against the interior wall of the esophagus 60 via additional structural features, such as a balloon, and may even be maintained against the interior wall via these structural features. In other or further embodiments, contact may be maintained between the support structure 130 and the esophagus 60 via one or more of surface tension (e.g., due to moisture on the esophagus wall), adhesives, and/or other suitable fixing elements. Certain of such alternative embodiments are discussed further below. As previously mentioned, the support structure 130 may also exhibit dielectric and/or heat conducting properties. In various embodiments, a support structure 130 having any of the foregoing properties can comprise one or more biocompatible materials, such as biocompatible plastics, such as, for example, one or more of polyethylene (PE), polypropylene (PP), nylon, or polyvinyl chloride (PVC). A thickness of the support structure 130 can be within a range of from about 0.001 inches to about 0.040 inches, or may be no greater than about 0.001, 0.002, 0.003, 0.004, 0.005, 0.010, 0.020, 0.030, or 0.040 inches.

The support structure 130 can be flexible, resiliently flexible, and/or compliant, e.g., in manners just described. Similarly, the encapsulated heat sensing structure can be flexible, resiliently flexible, and/or compliant. Accordingly, the heat sensor 120 can be flexible, resiliently flexible, and/or compliant. Flexibility of the heat sensor 120 may be about a single axis, in some embodiments, or the flexibility may be about multiple axes in other embodiments. For example, in some embodiments, the heat sensor 120 may extend longitudinally and may be flexible about any axis that is perpendicular to a longitudinal axis of the heat sensor 120. In this manner, the illustrated embodiment can be bent in any direction and may conform to longitudinal curves of the esophagus. In other or further embodiments, the heat sensor 120 can be flexible about the longitudinal axis itself and/or about any axis parallel thereto. For example, in the illustrated embodiment, the heat sensor 120 is also flexible in this manner, such that an outer surface of the heat sensor 120 is capable of conforming to an inner periphery of the esophagus 60. Stated otherwise, the heat sensor 120 can be flexible along its longitudinal length and/or in directions that are transverse to the longitudinal length. Accordingly, in various embodiments, the support structure 130 can be configured to conform to curves or bends along a length of the esophagus and/or to an inner periphery of the esophagus at any lateral cross-section of the esophagus.

With continued reference to FIGS. 3A and 3B, in various embodiments, the heat sensing region 170 can extend about a significant portion of a lateral cross-section of the heat sensor 120. The cross-sectional view of the heat sensor 120 shown in FIGS. 3A and 3B may generally be referred to as a "perimeter" of the heat sensor 120. In the illustrated embodiment, the perimeter is substantially circular in FIG. 3A and is substantially ovoid in FIG. 3B. The wires 142, 144 can create a bulge in the inner and outer layers 132, 134 of the sheath 130. The bulge may be exaggerated in the views shown in FIGS. 3A and 3B for purposes of illustration, as a diameter of the wires 142, 144 may be substantially smaller, in proportion to a diameter of the sheath 130, than what is shown in FIGS. 3A and 3B. In various embodiments, a diameter of the wires 142, 144 is no greater than about 0.0001, 0.001, or 0.010 inches, whereas a diameter of the sheath 130 can be within a range of from about 0.375 inches to about 1.25 inches, or no less than about 0.4, 0.5, 0.75, 1.0, or 1.25 inches.

As can be seen in FIGS. 3A and 3B, the wires 142, 144 extend about nearly the full perimeter of the sheath 130. In various embodiments, one or more wires extend along, or about, no less than ¼, ⅓, ½, ⅔, or ¾ of a perimeter of the sheath 130. Stated otherwise, the heat sensing region 170 can extend circumferentially about no less than ¼, ⅓, ½, ⅔, or ¾ of a perimeter of the sheath 130. As the sheath 130 may generally conform to an interior surface of the esophagus, the heat sensing region 170 likewise may extend circumferentially about no less than ¼, ⅓, ½, ⅔, or ¾ of, or about no less than a majority of, an inner perimeter of the esophagus 60.

Figure 4:
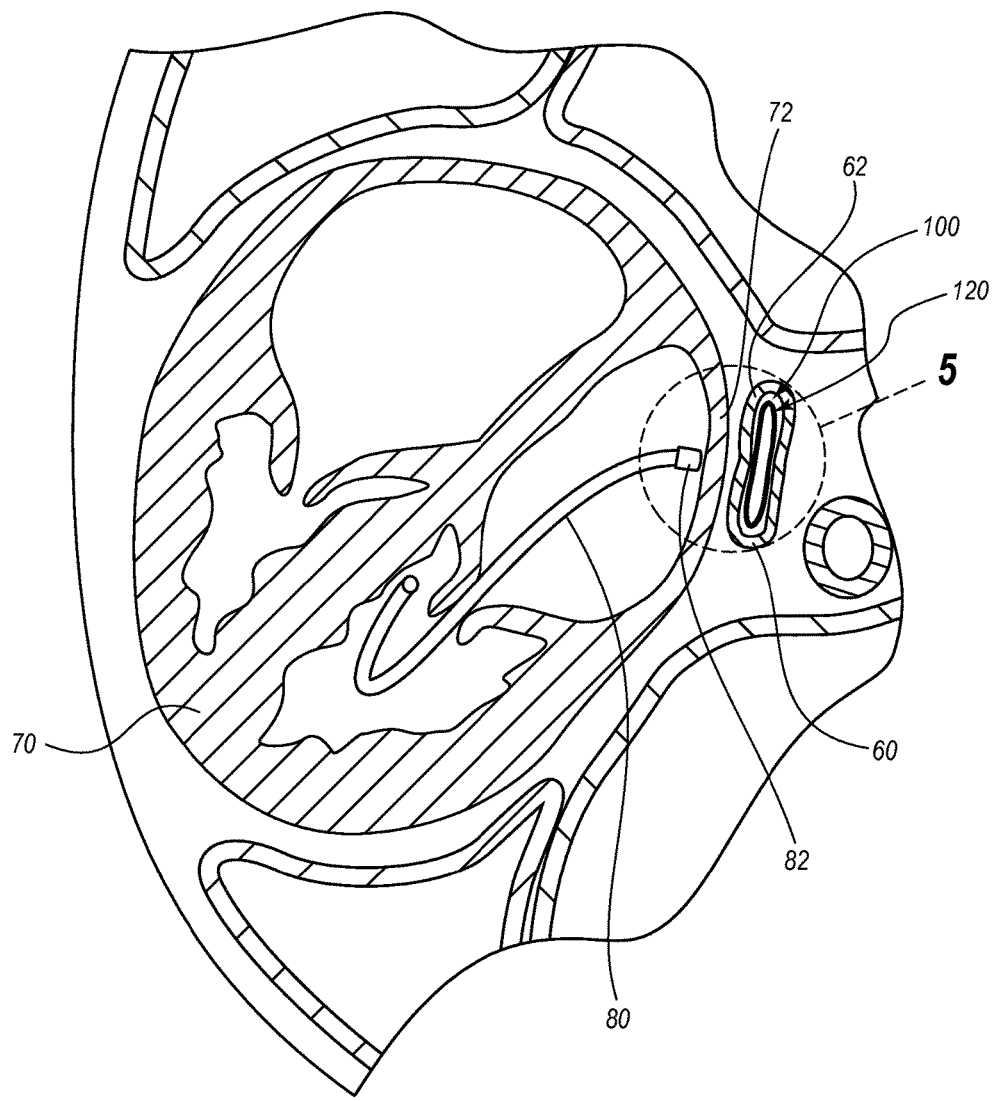
FIG. 4 is a cross-sectional view of the heat sensor of FIG. 1 positioned within the patient, taken along the view line 4-4 in FIG. 1.
Figure 5:
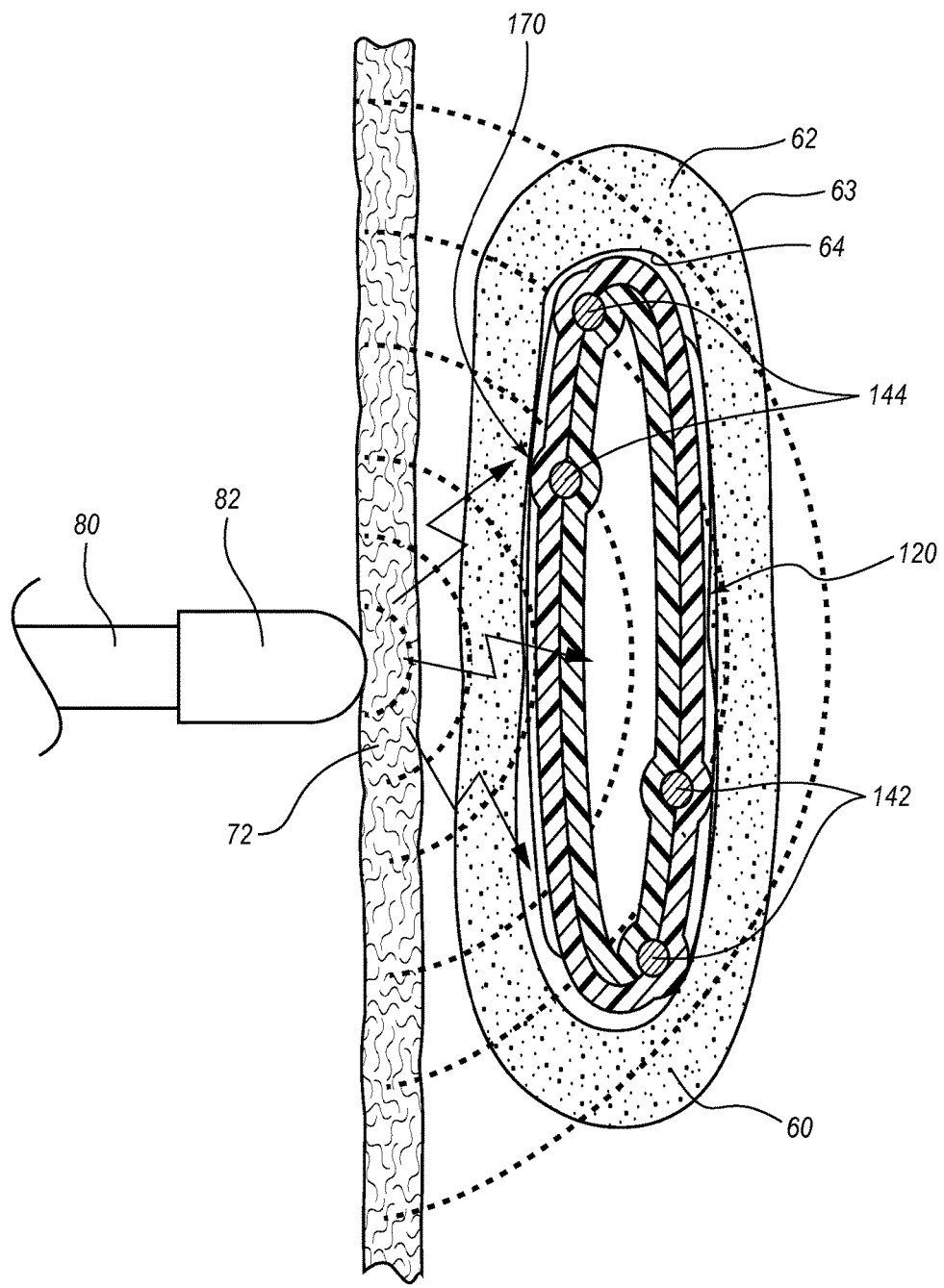
FIG. 5 is an enlarged view of FIG. 4, taken along the view line 5 therein, which includes a schematic depiction of heating of the atrial wall, the esophagus, and the heat sensor.

FIGS. 4 and 5 illustrate use of the heat sensor 120, and more generally, the heat sensing system 100, during an ablation procedure. In the illustrated embodiment, an ablation tool 80 delivers energy to the atrial wall 72 via an ablative tip 82. The energy causes heating of the atrial wall 72, as desired, but also can cause heating of the wall 62 of the esophagus 60. The heating may be more intense at an outer surface 63 of the esophagus wall 62, as compared with an inner surface 64 thereof, as the esophageal tissue can be insulating. In the illustrated arrangement, the wire 144 is positioned so as to more readily sense a change in temperature, as compared with the wire 142, although the wire 142 may nevertheless sense a less dramatic change in temperature. Cooling of the atrial wall 72 may proceed in a similar manner in cryoablation procedures.

Figure 6:
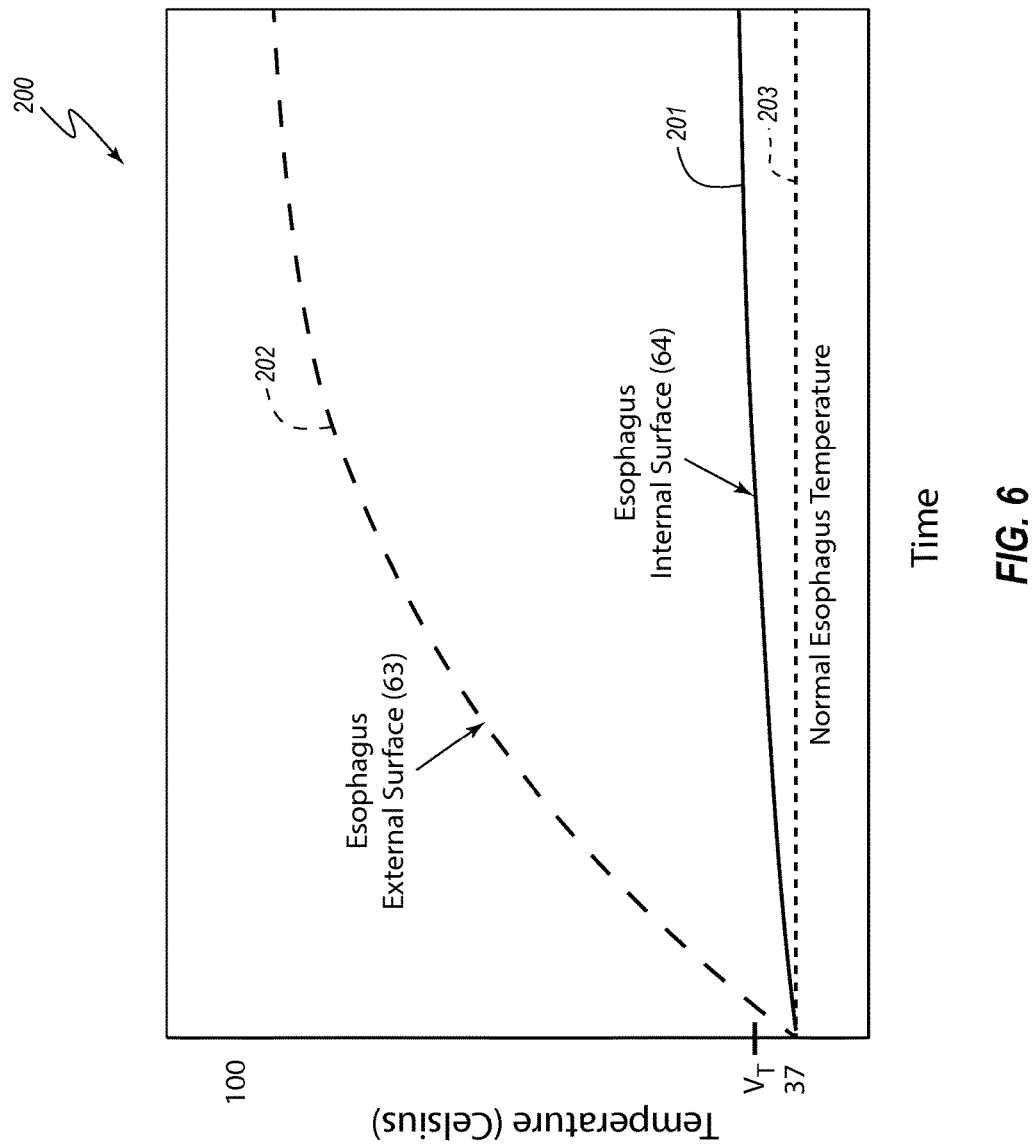
FIG. 6 is a plot that depicts illustrative heating patterns of different portions of the esophagus.

FIG. 6 depicts a plot 200 of a temperature profile 201 detected by the heat sensor 120 during an ablation procedure. More particularly, the plot depicts the temperature profile of the inner surface 64 of the esophagus 60, as detected by the wire 142 of the heat sensor 120, during the ablation procedure. In addition to the temperature profile 201, the plot 200 also includes, for reference purposes, a temperature profile 202 of the external wall 63 of the esophagus 60, as well as a baseline profile 203 that depicts the normal esophagus temperature. Comparison of the profiles 201, 202 illustrates how the esophagus can insulate the heat sensor 120 such that temperature changes are less pronounced at the position of the heat sensor 120. Accordingly, it can be desirable for the heat sensor 120 to be sensitive to small temperature changes.

In certain embodiments, the heat sensing system 100 triggers an alarm when the temperature profile 201 reaches or exceeds a threshold value $V_T$. The alarm can signify to the surgeon that damage to the esophagus and/or other bodily structures may result if ablation continues. The alarm may be provided in any suitable manner, such as via an audible sound and/or a visible warning on the display 104 (see FIG. 1). In other or further embodiments, ablation may automatically be discontinued when the threshold value $V_T$ is reached. For example, the controller 102 can direct that power no longer be supplied to the ablation tool 80 when the threshold value $V_T$ is reached. In still other or further embodiments, the alarm may be triggered and/or ablation automatically discontinued when the rate of change of the temperature profile 201 reaches or exceeds a threshold rate. The actual value of the threshold value $V_T$ may be different than what is schematically represented in FIG. 6.

Figure 7:
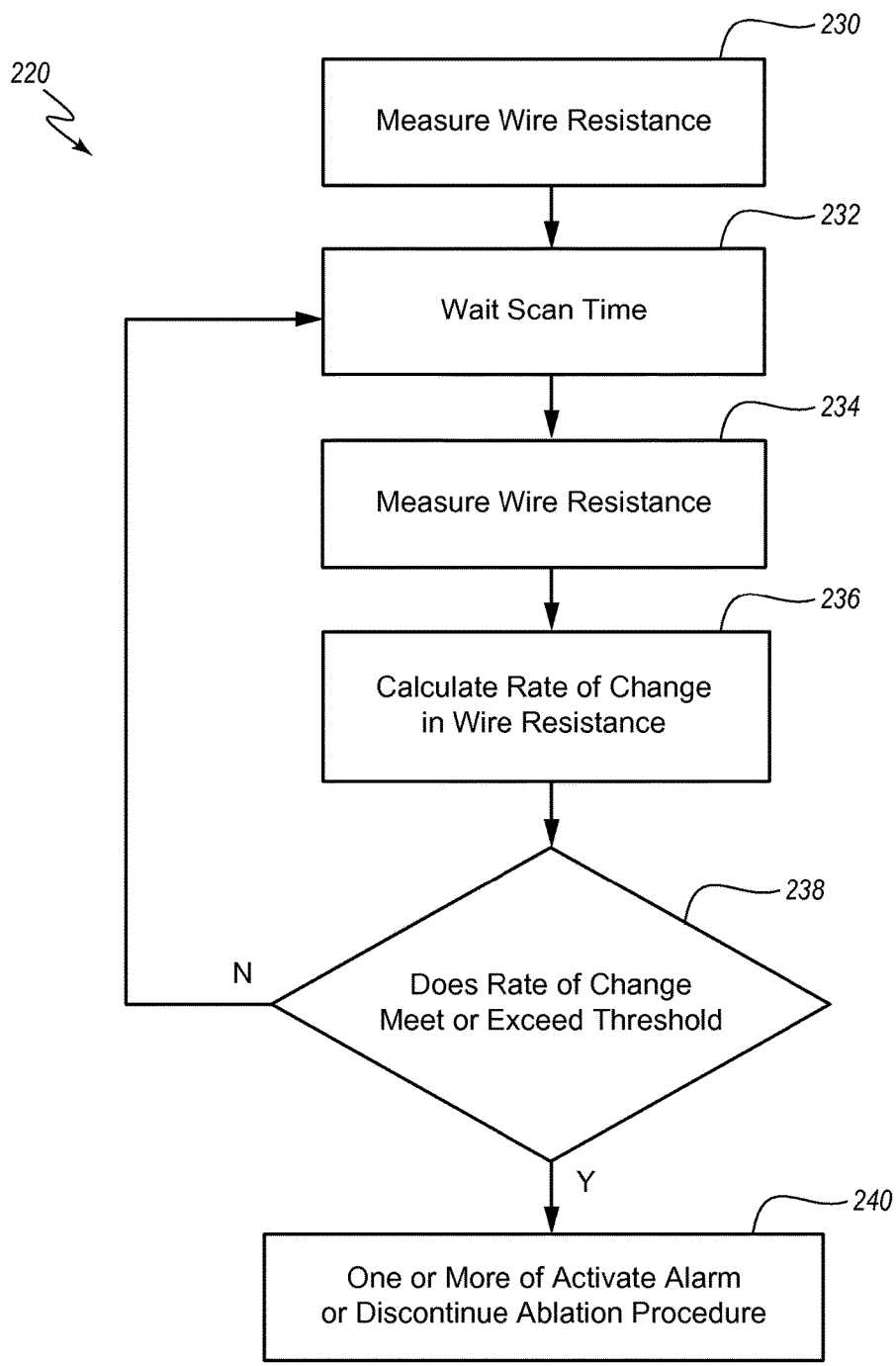
FIG. 7 is a flow diagram that depicts an illustrative method of using the heat sensing system of FIG. 1.

FIG. 7 depicts an illustrative method 220 of using the heat sensing system 100 of FIG. 1, such as during the ablation procedure depicted in FIG. 1. At least some of the stages of the method may be accomplished via the controller 102 and/or interaction between the controller 102 and the heat sensing assembly 110. At stage 230, the resistance of one or more wires 142, 144 is measured. At stage 232, a fixed period of time, which may also be referred to as a scan time, is permitted to transpire. In various applications, the scan time can be no greater than 0.01 seconds, 0.1 seconds, or 1 second. At stage 234, the resistance of the one or more wires 142, 144 is again measured. At stage 236, the rate of change in wire resistance is calculated. For example, stage 236 can comprise determining the difference in the wire resistances obtained at stages 230 and 234, and dividing the same by the fixed scan time to obtain the rate of change of the wire resistance. At decision stage 238, it is determined whether the rate of change meets or exceeds a threshold value. If it does not, then the process cycles back to stage 232. If the threshold value is met or exceeded, then the alarm is triggered at stage 240. Stage 240 may additionally or instead include automatically discontinuing the ablation. In some embodiments, the controller 102 includes electrical noise filters and/or is configured for redundant signal monitoring to prevent false alarms and/or undesired discontinuance of ablation.

Other methods of using the heat sensing system 100 are also contemplated, including variations of the method 220. For example, in some embodiments, measurements of the wire resistance may be substantially continuous. Accordingly, stage 232, at which an increment of time is permitted to transpire between subsequent measurements of wire resistance, may be eliminated. The rate of change of wire resistance may be calculated by comparing any desired subset of measurements, taking into account the amount of time that transpired between the measurements.

Figure 8A:
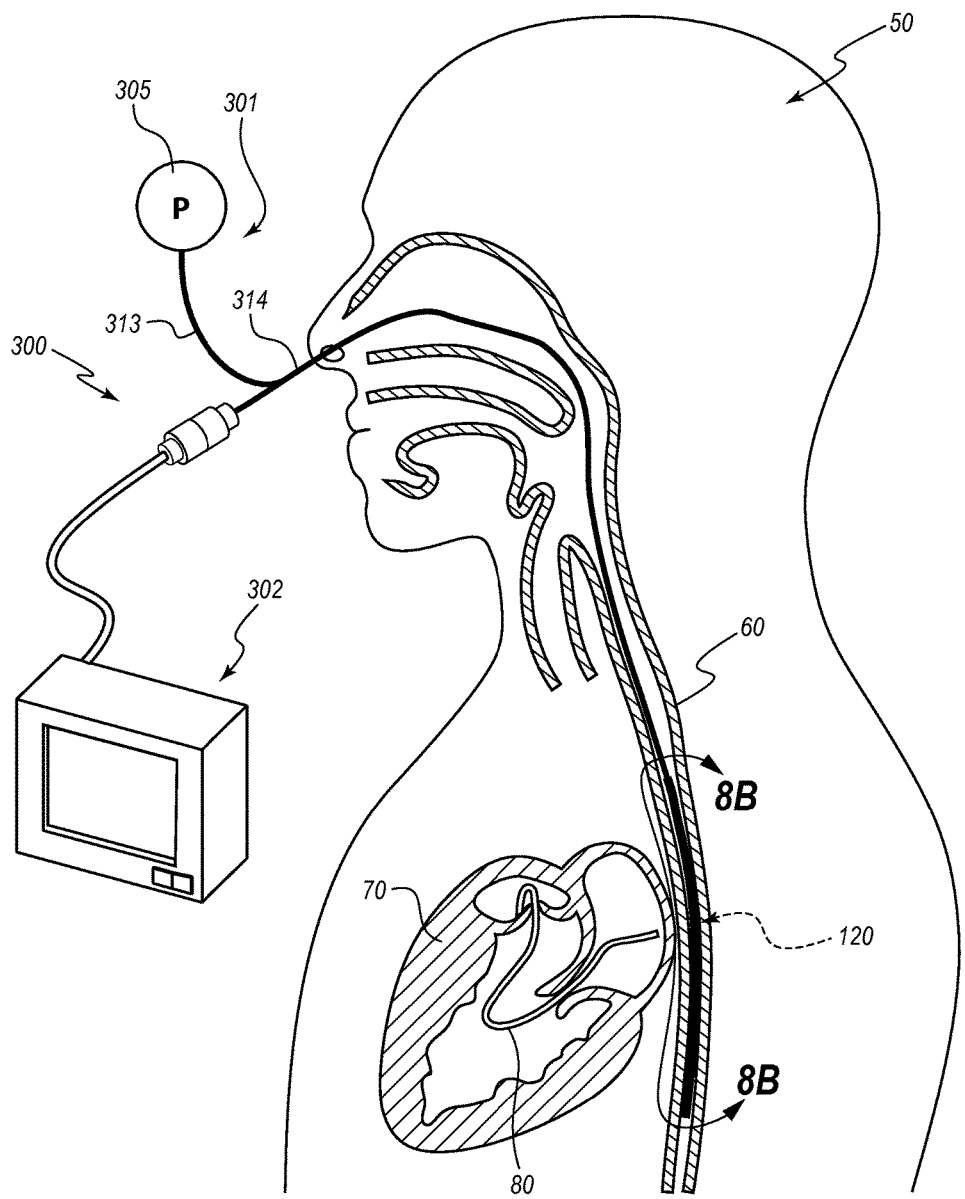
FIG. 8A is a perspective view of another embodiment of a heat sensing system that includes an inflation system for placement or deployment of the heat sensor within the patient, wherein an elevation view of the heat sensor is depicted in a packaged or undeployed state within the esophagus of the patient.

FIG. 8A illustrates another embodiment of a heat sensing system 300 that can resemble the heat sensing system 100 described above in certain respects. Accordingly, like features are designated with like reference numerals, with the leading digits incremented to "3." Relevant disclosure set forth above regarding similarly identified features thus may not be repeated hereafter. Moreover, specific features of the system 300 may not be shown or identified by a reference numeral in the drawings or specifically discussed in the written description that follows. However, such features may clearly be the same, or substantially the same, as features depicted in other embodiments and/or described with respect to such embodiments. Accordingly, the relevant descriptions of such features apply equally to the features of the system 300. Any suitable combination of the features and variations of the same described with respect to the system 100 can be employed with the system 300, and vice versa. This pattern of disclosure applies equally to further embodiments depicted in subsequent figures and described hereafter, wherein the leading digits may be further incremented.

The heat sensing system 300 can include the heat sensor 120 discussed above. The heat sensing system 300 can further include an inflation system 301 configured to deploy the temperature sensor 120 within the esophagus 60 of the patient 50. In some embodiments, the heat sensing system 300 includes a monitor 302, such as the monitor 102 discussed above, which may include additional functionalities, such as the ability to sense, monitor, control, and/or display the pressure of an inflation fluid.

The inflation system 301 can include any suitable inflation device 305, such as, for example, those that are commonly used to deploy stents or the like. In some embodiments, the inflation device 305 can include a syringe that delivers inflation fluid to a fluid path 313 and can pressurize the fluid within the fluid path 313. It is noted that the term "fluid" may refer to one or more liquids and/or gases. The fluid path 313 can be incorporated into a catheter 314, such as the catheter 114 discussed above. For example, in some embodiments, the fluid path 313 includes one or more lumens that pass through at least a portion of the catheter 114. In other embodiments, the fluid path 313 may be separate from the catheter 114. For example, in some embodiments, a conduit that is separate from the catheter 114 may define the fluid path 313. The separate conduit may be movable relative to the catheter 114, and may be placed within the esophagus 60 separately from the catheter 114 and/or separately extracted from the esophagus 60.

In some embodiments, the inflation device 305 is configured to be controlled by the controller 302. For example, in some embodiments, a pressure sensor (e.g., a pressure transducer) can be couple to the fluid path 313 and can be in electrical communication with the controller 302. Based on pressure readings from the pressure sensor, the controller 302 can adjust the inflation device 305 to increase or decrease the pressure within the fluid path 313.

Figure 8C:
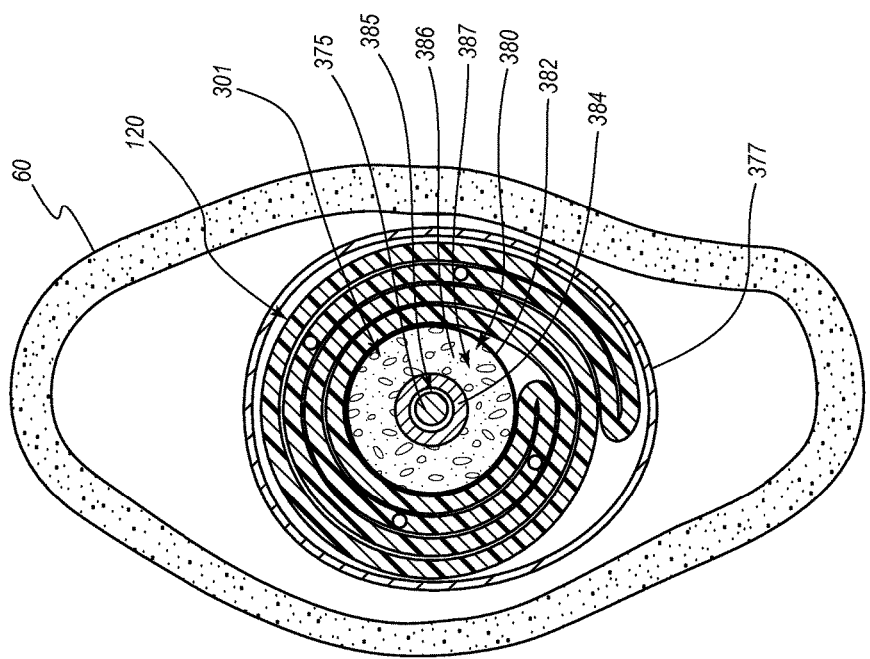
FIG. 8C is a cross-sectional view of the heat sensor and the portion of the inflation system within the esophagus of the patient taken along the view line 8C-8C in FIG. 8B.
Figure 8B:
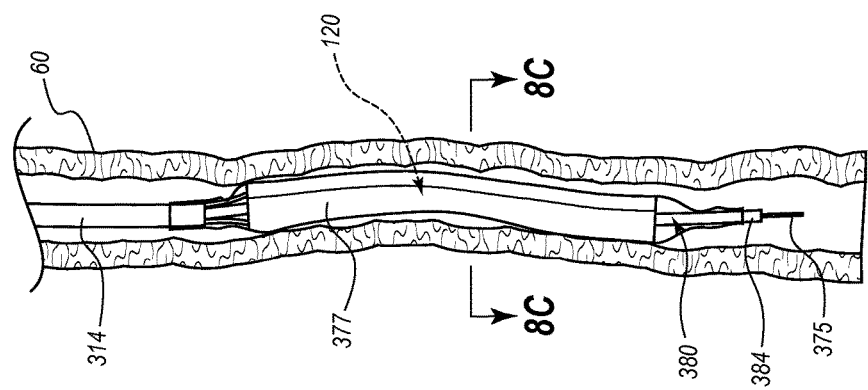
FIG. 8B is an enlarged view of the heat sensor and a portion of the inflation system within the esophagus of the patient taken along the view line 8B-8B in FIG. 8A.

FIGS. 8B and 8C illustrate the heat sensor 120 in a packaged, undeployed, folded, rolled, or compressed state, which facilitates insertion of the heat sensor 120 into the esophagus 60. In the illustrated embodiment, the heat sensor 120 includes a support structure 130 that has a substantially cylindrical natural configuration; however, the support structure 130 is folded and rolled into a low-profile configuration and is maintained in this configuration via a removable packaging sheath 377.

The inflation system 301 includes an inflation assembly 380 that is positioned at an interior of the heat sensor 120. The inflation assembly 380 includes an expandable balloon 382 and a wire sheath 384. The wire sheath 384 defines a lumen 385 that is sized to pass over a guide wire 375. A cavity 387 is provided between the balloon 382 and the wire sheath 384, which can be filled and pressurized with an inflation fluid 386. At the stage depicted in FIGS. 8A-8C, only a small amount of inflation fluid 386 is present within the balloon 380. In other embodiments, no inflation fluid 386 may be present within the balloon 380 at the illustrated stage.

Placement of the heat sensor 120 into the position shown in FIGS. 8A-8C can proceed as follows. The guide wire 375 is inserted into the esophagus 60 and advanced to a desired position, which may be substantially below the position at which the esophagus 60 is closest to the heart 70. The packaged heat sensor 120 and inflation assembly 380 are then advanced over the guide wire 375, with the wire sheath 384 sliding or otherwise passing over the guide wire 375. The packaging sheath 377 may then be removed.

Figure 9A:
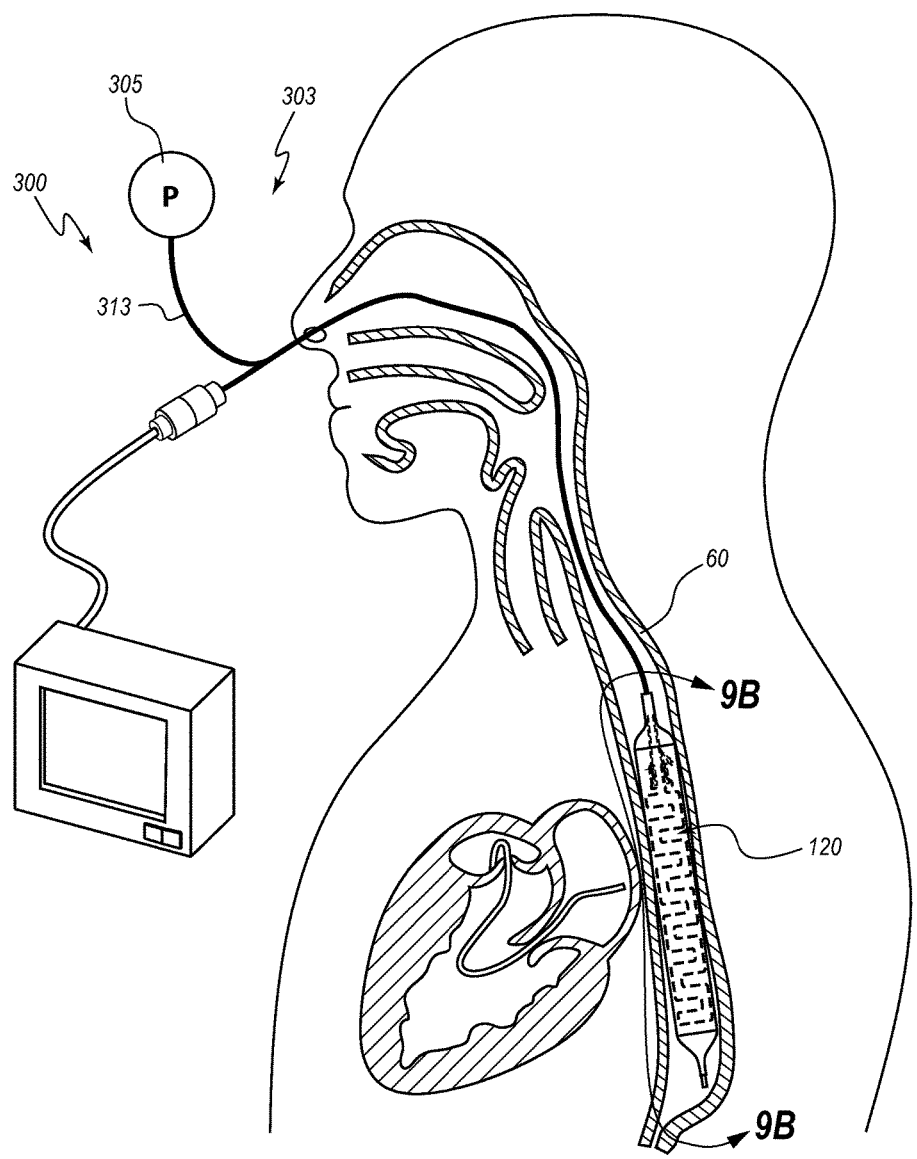
FIG. 9A is an elevation view of the heat sensing system of FIG. 1 being used in conjunction with the inflation system of FIG. 8A, wherein the heat sensor is depicted in an unpackaged or deployed state.
Figure 9C:
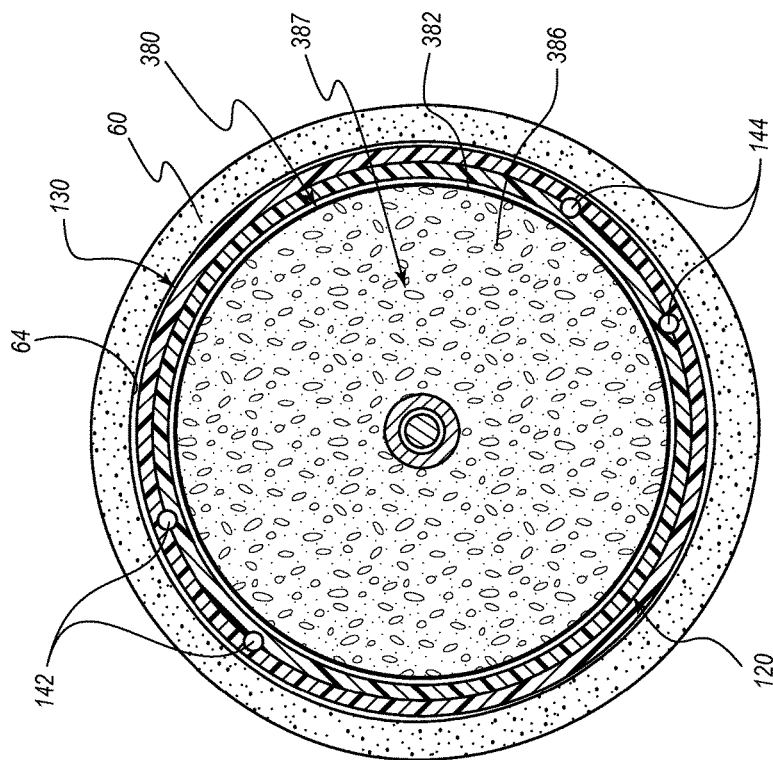
FIG. 9C is a cross-sectional view of the heat sensor and the portion of the inflation system within the esophagus of the patient taken along the view line 9C-9C in FIG. 9B.
Figure 9B:
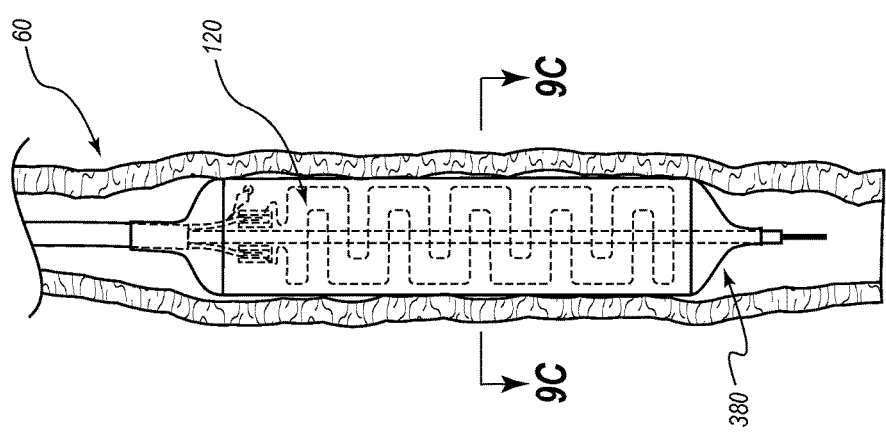
FIG. 9B is an enlarged view of the heat sensor and a portion of the inflation system within the esophagus of the patient taken along the view line 9B-9B in FIG. 9A.

FIGS. 9A-9C illustrate a subsequent stage of placement of the heat sensor 120 within the esophagus 60. At this stage, the inflation device 305 is used to introduce additional inflation fluid 386 into the balloon 382, thereby causing the balloon 382 to expand. The balloon 382 may be expanded sufficiently far, or by a sufficient amount, to bring the support structure 130 into contact with and/or otherwise into close proximity to the inner surface 64 of the esophagus 60. The heat sensor 120 may be said to be in a deployed or expanded state in FIGS. 9A-9C.

Figure 10B:
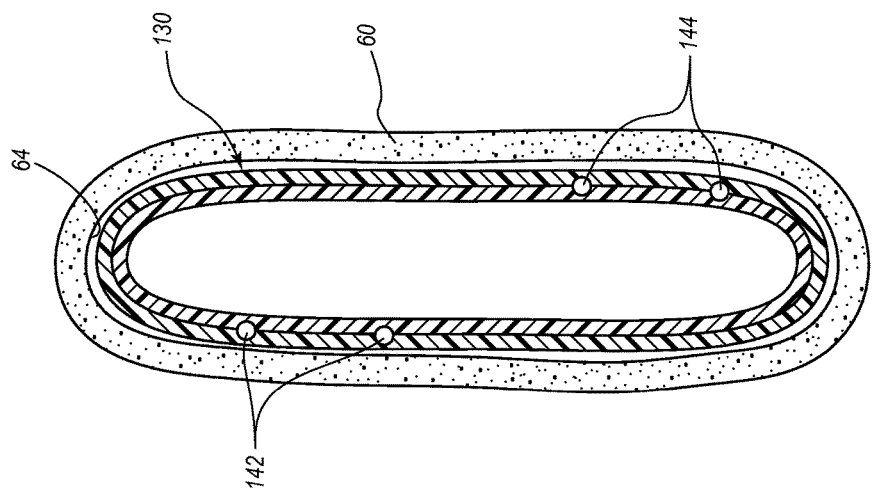
FIG. 10B is a cross-sectional view of the heat sensor of FIG. 1 within the esophagus of the patient taken along the view line 10B-10B of FIG. 10A.
Figure 10A:
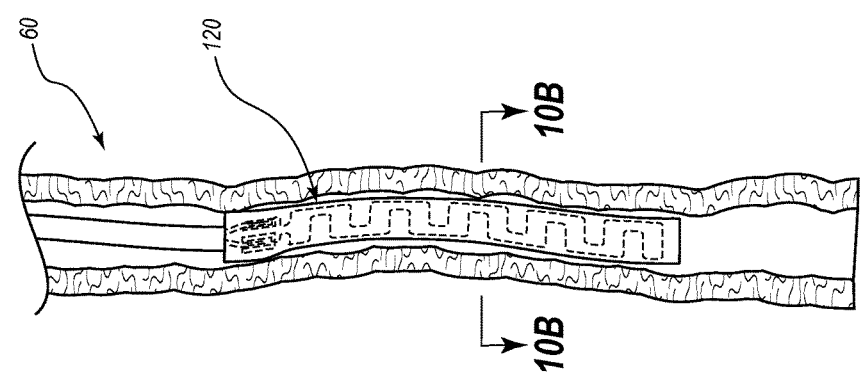
FIG. 10A is another elevation view of the heat sensor of FIG. 1 within the esophagus of the patient (shown in cross-section) after having been deployed within the esophagus and the inflation system removed from it, such that the sensor remains in the unpackaged or deployed state and is further in a compliance state so as to yield to movement of the esophagus.

FIGS. 10A and 10B illustrate a subsequent stage of placement of the sensor 120, in which the heat sensor 120 is in the desired position and is in an operational state, so as to be used during an ablation procedure. The inflation assembly 380 has been removed from an interior of the heat sensor 120, and the esophagus 60 has returned to its relaxed or natural orientation. In the illustrated embodiment, the support structure 130 is biased outwardly so as to maintain contact with and/or close approximation to the inner surface 64 of the esophagus 60. In other or further embodiments, the support structure 130 may maintain contact with and/or close approximation via surface tension or other suitable methods or manners of adhesion, as discussed above. In the illustrated configuration, the heat sensor 120 is still in the deployed or expanded state. However, as it is also now free to be moved by movement of the esophagus 60, or otherwise conform to the esophagus 60, it may also be referred to as being in a conformance, tracking, following, or according state. The support structure 130 may be sufficiently compliant or flimsy to remain in close proximity to the inner surface 64 of the esophagus substantially without deforming the esophagus. The heat sensor 120 may detect temperature changes and/or otherwise operate in manners such as described above.

In other embodiments, the inflation assembly 380 may remain at the interior of the heat sensor 120 during the ablation procedure. A pressure of the expansion fluid within the balloon 382 can be adjusted to maintain the heat sensor 120 in contact with the esophagus without expanding the esophagus. Rather, the pressure can be adjusted to a level at which the heat sensor 120 tracks the natural movement of the esophagus. Such a tracking state is similarly discussed below with respect to FIG. 12C.

In still other embodiments, the heat sensor 120 can be deployed within the esophagus 60 without the inflation assembly 380. For example, in some embodiments, the heat sensor 120 can be positioned within the esophagus 60 over a guidewire while being retained in the packaging sheath 377. Or in other or further embodiments, the heat sensor 120 can be selectively positioned within the esophagus 60 and released from the end of a cannula. In either case, whether upon removal of the sheath 377 or release from the cannula, a resilience of the wall material of the heat sensor 120 can cause the sensor to unroll, unfold, or otherwise expand and position itself against the wall 62 of the esophagus 60. In some embodiments, although the sensor 120 is sufficiently resilient to expand so as to conform to an inner surface 64 of the esophagus 60, it may nevertheless track the movement of the esophagus and/or not substantially expand the esophagus.

FIGS. 11A and 11B illustrate another embodiment of a heat sensor 420, which is compatible with the heat sensing system 300 of FIG. 8A. The heat sensor 420 can function in a manner similar to the inflation assembly 380 discussed above, and thus may also be referred to as an inflation assembly. For example, the heat sensor 420 can include a support structure 430 similar to the support structure 130 discussed above, but which can also function in a manner similar to the balloon 182 discussed above. The support structure 430 can define at least a portion of a closed cavity 487 into which inflation fluid can be received to expand the support structure 430 into close proximity to (e.g., contact with) an inner wall of the esophagus. The heat sensor 420 can be assembled to a catheter 414, such as the catheter 314 discussed above.

The illustrated embodiment of the heat sensor 420 includes two wires 442, 444, such as the wires 142, 144 (only wire 442 is shown in FIG. 11A for clarity). Other embodiments can include more or fewer wires in manners such as previously discussed. The illustrated wires 442, 444 can be connected to electrical leads 415 at connection interfaces 445. The heat sensor 420 can include a thermocouple 472, such as the thermocouple 172 described above. The wires 442, 444 may be sandwiched between inner and outer dielectric layers 432, 434 of the support structure 430, and the heat sensor 420 can further include a wire sheath 484 at an interior of the support structure 430. As shown in FIG. 11A, the proximal and distal ends of the support structure 430 can be attached to the wire sheath 484 via proximal and distal fluid-tight seals 489. Accordingly, the closed cavity 487 can be defined by the support structure 430 and the wire sheath 484, which are sealed to each other via the fluid-tight seals 489.

FIGS. 12A-12C depict various stages of positioning the heat sensor 420 within the esophagus 60 of the patient. At the stage depicted in FIG. 12A, the heat sensor 420 is in a packaged state within a packaging sheath 477. In some embodiments, the wire sheath 484 is advanced over a guide wire 475 into the position shown in FIG. 12A. In the illustrated embodiment, the guide wire 475 is removed before progressing to subsequent stages of delivery. In other embodiments, the guide wire 475 may remain in place during greater amounts of the placement and/or heat sensing procedures. At the stage depicted in FIG. 12B, an inflation fluid 486 is introduced into the cavity 487 and thereby expands the support structure 430 into contact and/or close proximity with the esophagus 60. The heat sensor 420 is thus in an expanded or deployed state. The guide wire 475 has been removed at this stage. At the stage depicted in FIG. 12C, the inflation fluid 486 remains within the support structure 430. However, the pressure of the inflation fluid 486 has been reduced, as compared with the inflation fluid at the stage of FIG. 12B. The reduced pressure can allow the support structure 430 to comply with the natural configuration of the esophagus 60. Accordingly, the configuration shown in FIG. 12C may be referred to as a conformance, tracking, following, or according state. As will be apparent from the discussion above regarding the inflation device 305, in some embodiments, the pressure of the inflation fluid 486 can be controlled by the inflation device 305. In some embodiments, the inflation device 305 can be controlled manually. In other embodiments, the inflation device 305 can be controlled by a controller in manners such as described above, and thus a pressure of the inflation fluid 486 can be controlled by the controller.

In some embodiments, expanding the support structure 430 by an amount sufficient to displace a portion of the esophagus 60, such as in the manner depicted in FIG. 12B, can aid in achieving a tight fit or contact between the support structure 430 and the esophagus. For example, this inflation stage can allow the support structure 430 to adhere to the inner surface 64 of the esophagus 60, such as by surface tension, by an adhesive coated on the exterior of the support structure 430, and/or in any other suitable manner. Thereafter, when the pressure of the inflation fluid 486 is reduced, the support structure 430 can maintain its close proximity with the inner surface 64 of the esophagus. Such a close proximity can aid with thermal transfer from the esophagus 60 to the heat sensing wires 442, 444. In some arrangements, it can be desirable to ensure that the inflation pressure is reduced to an amount such as depicted in FIG. 12C prior to commencing ablation of the atrial wall 72, as the unexpanded or slack orientation of the esophagus 60 may provide greater spacing between the atrial wall 72 and the esophagus 60.

Figure 13:
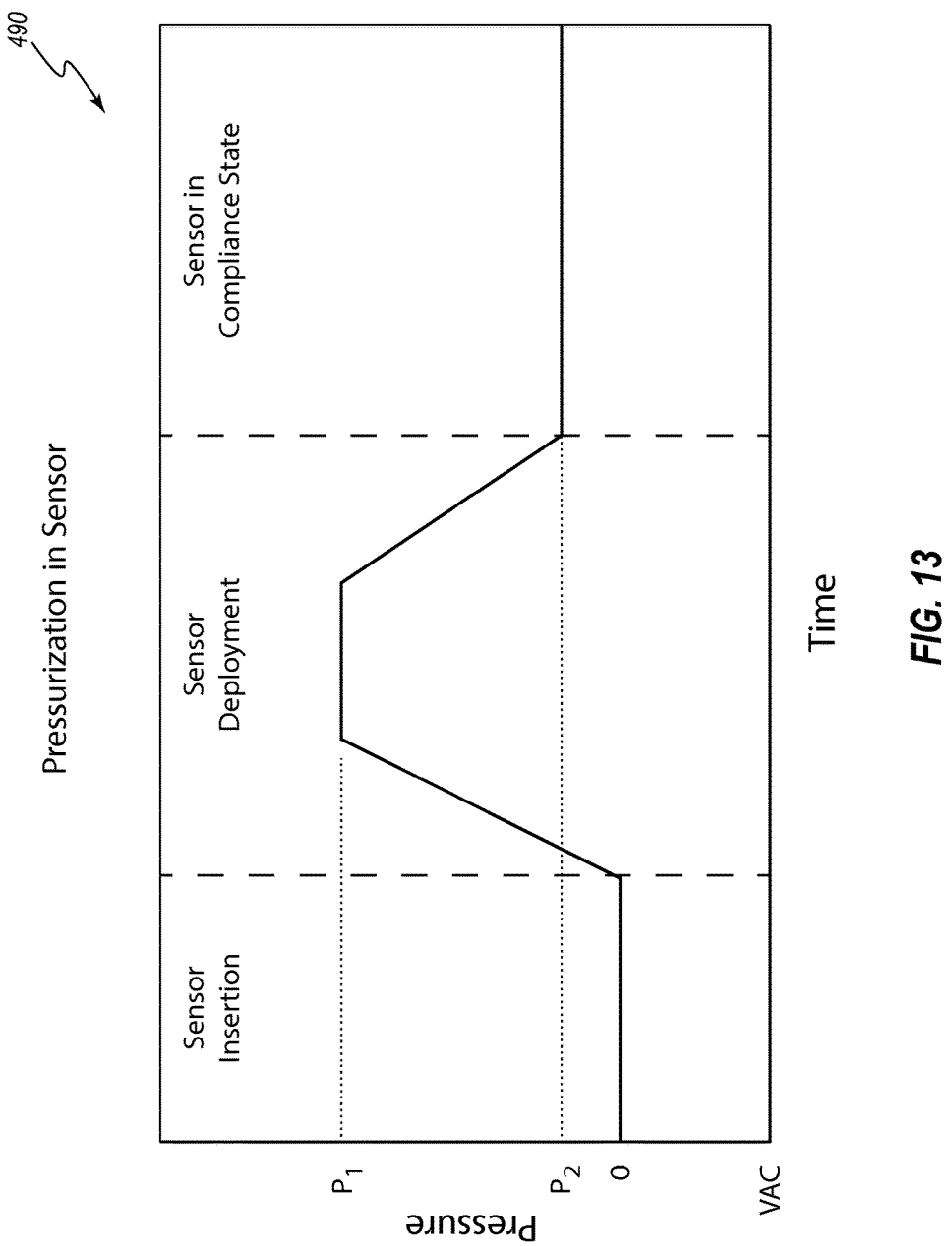
FIG. 13 is a plot of a pressure profile within the sensor of FIG. 11A during different stages of use.

FIG. 13 depicts a plot 490 of the pressure of the inflation fluid 486 as a function of time. The three deployment stages depicted in FIGS. 12A-12C are identified in the plot 490 as "Sensor Insertion," "Sensor Deployment," and "Sensor in Compliance State." During sensor insertion, only atmospheric pressure may be present within the support structure 430. During deployment, the inflation fluid 486 can increase the pressure to a value of $P_1$. Thereafter, the inflation fluid 486 can be reduced to a tracking pressure $P_2$. The tracking pressure $P_2$ can be sufficient to maintain contact between at least a portion of the support structure 430 and the esophagus wall, and yet not substantially deform the esophagus wall.

Figure 14:
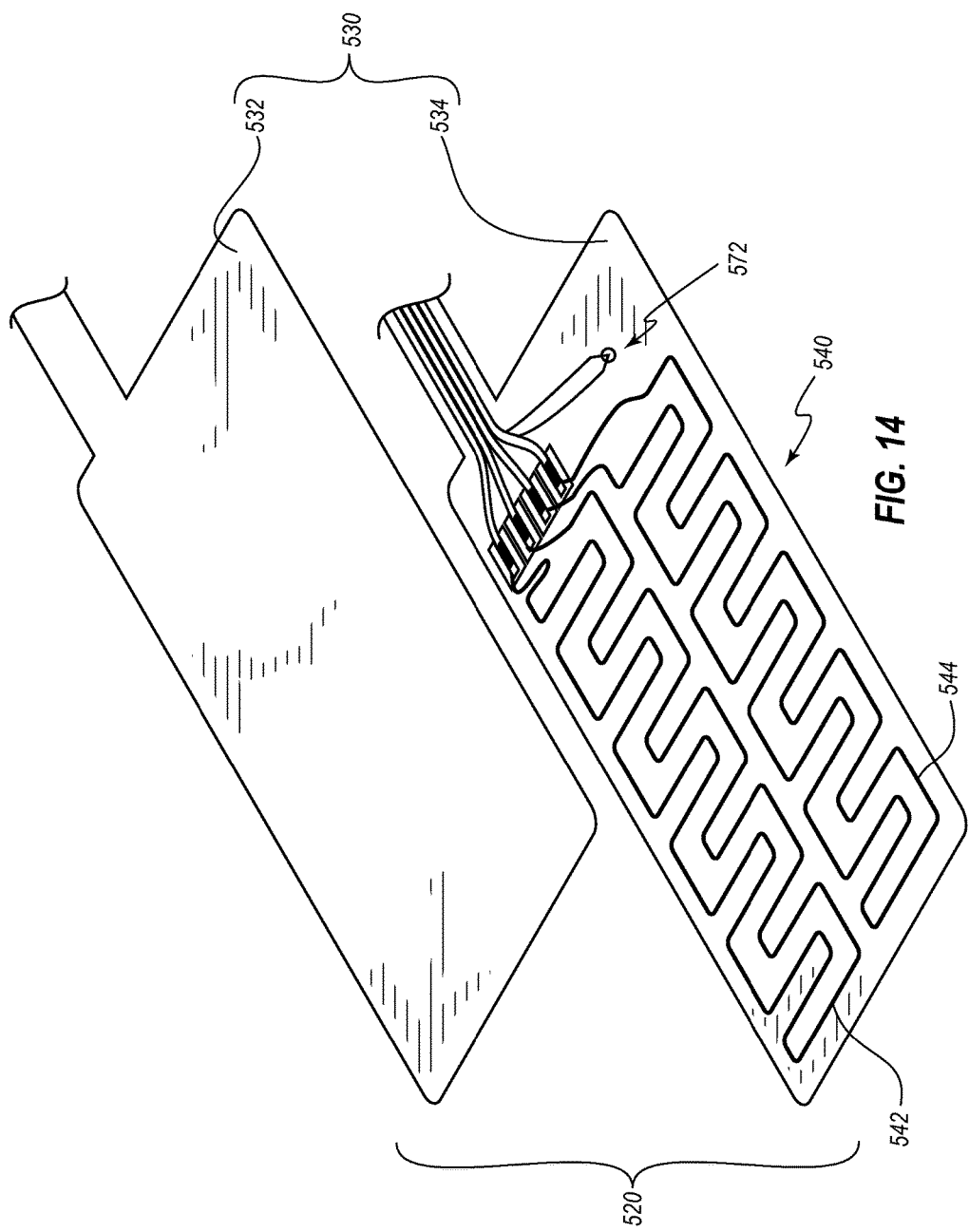
FIG. 14 is an exploded perspective view of another embodiment of a heat sensor compatible with the heat sensing system of FIG. 8A.
Figure 15:
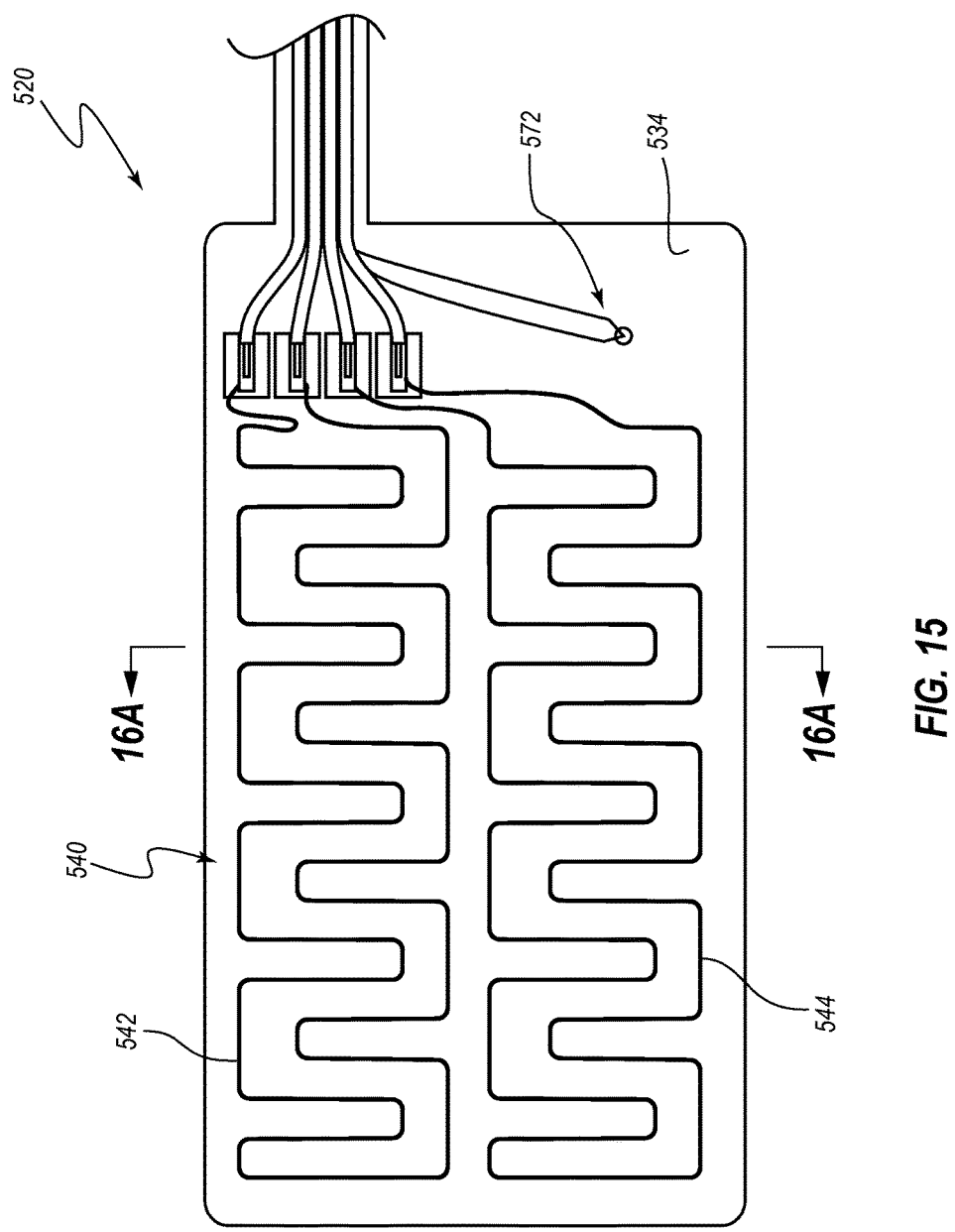
FIG. 15 is a plan view of a portion of the heat sensor of FIG. 14.

FIGS. 14 and 15 illustrate another embodiment of a heat sensor 520. The heat sensor 520 includes a heat sensing structure 540, which is defined by two wires 542, 544. More or fewer wires may be used, in manners such as described above. The heat sensor 520 further includes a reference temperature sensor 572. The reference temperature sensor 572 may also be referred to herein as a thermocouple 572, although any suitable temperature sensor may be used. The wires 542, 544 and the thermocouple 572 can be laminated or sandwiched between two or more layers of support material 532, 534, which may also be referred to as a superstrate 532 and a substrate 534, respectively. The superstrate 532 and the substrate 534 can cooperate to form a support structure 530. In FIG. 15, the superstrate 532 is not shown. The support structure 530 can be substantially flat or planar when in a relaxed or natural state.

As discussed above with respect to the temperature sensor 172, the temperature sensor 572 can be configured to track a temperature that is representative of an entirety of the substrate 534 and/or superstrate 532 to which it is attached. The wires 542, 544 can be configured to sense localized heating.

Figure 16A:
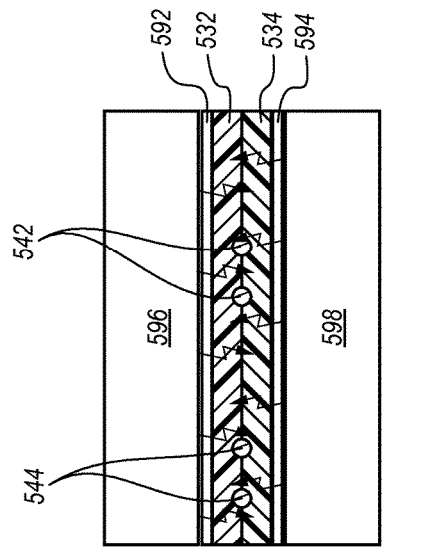
FIG. 16A, FIG. 16B, and FIG. 16C each depict a different stage of a method of forming the heat sensor of FIG. 14.
Figure 16B:
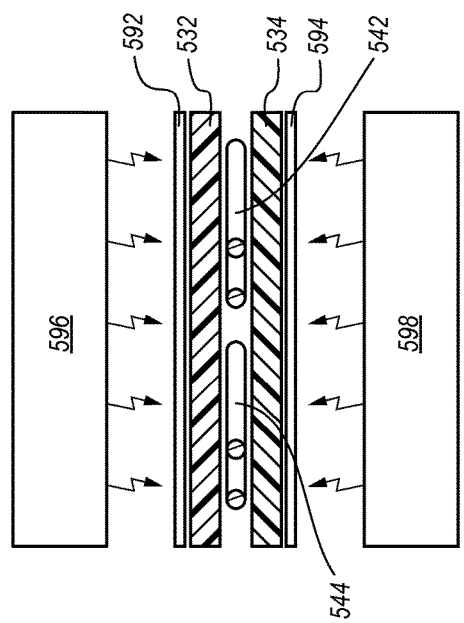
Figure 16C:
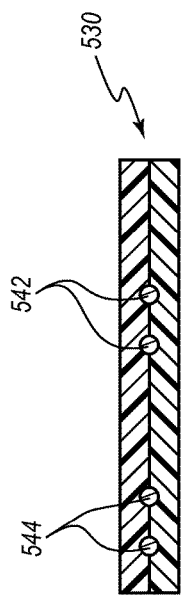

FIGS. 16A-16C depict an illustrative method for assembling the heat sensor 520. In some embodiments, two separate wires 542, 544 and a reference thermocouple 572 (see FIG. 15) are positioned on one side of a thin flexible plastic film 534. A second thin flexible plastic film 532 is positioned opposite the first film 534, and the components are placed between two heat plates 596, 598, which cause heat lamination and bonding of the films 532, 534 to each other with the components captured inside and sealed around the perimeter. In some methods, non-stick films 592, 594 are placed between the heat plates 596, 598 and the films 532, 534. The non-stick films 592, 594 may comprise, for example, sheets of polytetrafluoroethylene. The heat plates 592, 594 are approximated together under a load of any suitable amount and for a suitable duration until the thin films 532, 534 adhere to each other. Other methods of containing, capturing, or encapsulating the wires 542, 544 between the thin films 532, 534, or providing a dielectric barrier between the sensing wires 532, 534 and the esophagus 60, are contemplated, such as, for example, one or more of adhesives, plastic coatings, or mechanical seals. However, in some embodiments, lamination of one or more wires between sheets of plastic can be particularly useful where the wires are not amenable to being preformed to a predetermined shape (e.g., due to a small diameter).

FIGS. 17A-17C depict various stages of positioning the heat sensor 520 within the esophagus 60 of the patient. At the stage depicted in FIG. 17A, the heat sensor 520 is in a packaged state within a packaging sheath 577. At the stage depicted in FIG. 17B, an inflation assembly 580 is expanded so as to move the support structure 530 into contact and/or close proximity with the esophagus 60. The heat sensor 520 is thus in an expanded or deployed state at this stage. At the stage depicted in FIG. 17C, the inflation assembly 580 has been removed. In the illustrated embodiment, opposing side ends of the support structure 530 overlap one another when the sensor 520 has been positioned within the esophagus 60. Such an arrangement can allow for the heat sensor 520 to be used with any of a variety of patients whose anatomies differ, such that their esophagi define differently sized inner perimeters. For example, in smaller esophagi, the opposing side ends of the support structure 530 may overlap to a greater degree, whereas in larger esophagi, the opposing side ends of the support structure 530 may not overlap. In any of the foregoing instances, whether or not the opposing side ends of the support structure 530 overlap, the support structure may be said to form a tube, sleeve, or sheath, which can extend along at least a portion of an inner perimeter of the esophagus. In various embodiments, the rolled, coiled, or curved support structure 530 may cover no less than about ¼, ⅓, ½, ⅔, or ¾ of, or no less than a majority of, the inner perimeter of the esophagus, and in instances where the side ends abut one another or overlap, can cover an entirety of the inner perimeter. In each case, a lateral cross-section of the support structure 530, such as that shown in FIG. 17C, can be said to depict the lateral perimeter of the support structure 530. Stated otherwise, the term "perimeter" does not necessarily refer to a closed loop, and can define a lateral length (e.g., arc length) of a non-closed tube, sleeve, or sheath structure.

In instances where the side ends overlap, a width of the support structure 530, as measured between opposing side edges of the support structure 530, may exceed the value of the perimeter (e.g., the circumference) of the inner surface of the esophagus. In some arrangements, overlapping side ends, such as those depicted in FIG. 17C, may allow for the heat sensor 520 to yield more readily to movements of the esophagus 60, as compared with a closed tube. As can be appreciated from the drawings, in the illustrated embodiment, the heat sensor 520 is flexible about at least a longitudinal axis. In some embodiments, the heat sensor 520 is also flexible about axes that are perpendicular to the longitudinal axis, such that the heat sensor 520 can conform to any longitudinal curvature of the esophagus.

FIG. 18 illustrates another embodiment of a heat sensor 620. The heat sensor 620 includes a heat sensing structure 640, which includes a plurality of thermocouples 672 that are spread out in an array. The heat sensing structure 640 can define a heat sensing region 670. Each thermocouple 672 can be configured to sense a temperature at a point within the heat sensing region 670. Any suitable arrangement of electrical leads 615 can run from the sensing region of each thermocouple 672 to a connector or other device, such as the connector 112 described above, so as to interface with a monitor (e.g., the controller 102). The thermocouples 672 and associated leads 615 can be sandwiched between two layers of support material 632, 634, which forms a support structure 630. The support structure 630 can be substantially planar when in a natural or relaxed state.

FIGS. 19A and 19B illustrate the heat sensor 620 positioned within the esophagus 60. The support structure 630 can be coiled such that opposing side ends of the support structure 630 overlap one another. The array of thermocouples 672 can be used to obtain numerous temperature measurements so as to monitor the portion of the esophagus 60 that is adjacent to the heat sensing region 670.

The heat sensor 620 can be delivered into the esophagus 60 in any suitable manner. For example, in some embodiments, the heat sensor 620 is introduced into the esophagus 60 in a packaged state in which the heat sensor 620 is rolled or coiled into a small cross-sectional profile within a packaging sheath, such as the packaging sheath 377 discussed above.

Figure 20B:
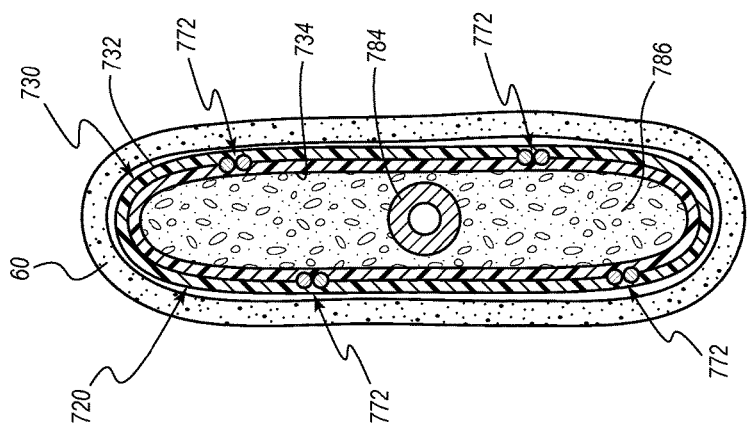
FIG. 20B is another cross-sectional view of the heat sensor of FIG. 20A positioned within the esophagus of a patient taken along the view line 20B-20B in FIG. 20A.
Figure 20A:
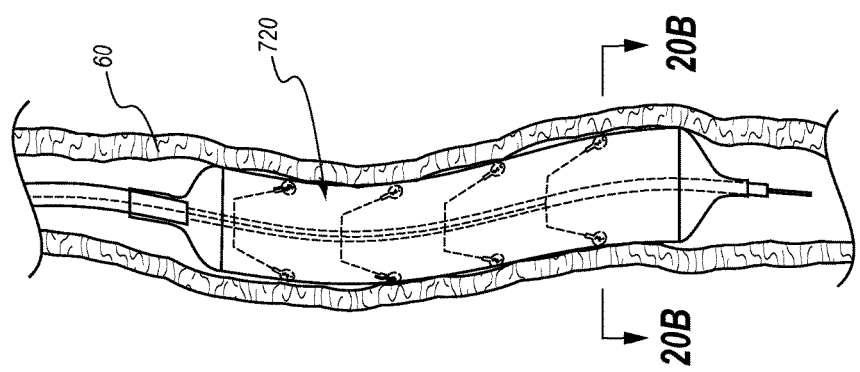
FIG. 20A is a cross-sectional view of another embodiment of a heat sensor positioned within the esophagus of a patient.

FIGS. 20A and 20B illustrate another embodiment of a heat sensor 720. The heat sensor 720 includes a heat sensing structure, such as the heat sensing structure 540 shown in FIG. 18, which includes a plurality of thermocouples 772 that are spread out in an array. The thermocouples 772 and their associated electrical leads can be sandwiched between two layers of support material 732, 734, which forms a support structure 730. Unlike the support structure 630, the support structure 730 may form a closed loop, which is sized so as to rest against an inner surface of the esophagus 60. In the illustrated embodiment, the heat sensor 720 can resemble the inflatable heat sensor 420 depicted in FIGS. 11A-12C, and may include a wire sheath 784. The support structure 730 may be maintained in a conformance operational mode by slightly pressurized inflation fluid 786 in manners such as described above. In other embodiments, the heat sensor 720 may be separate from the inflation fluid 786 so as not to directly contact the fluid. For example, in some embodiments, the heat sensor 720 may be urged into place by a separate expandable balloon, such as the balloon 382 discussed above. Any other suitable deployment techniques and properties, such as those discussed above, are possible for the heat sensor 720.

Figure 21C:
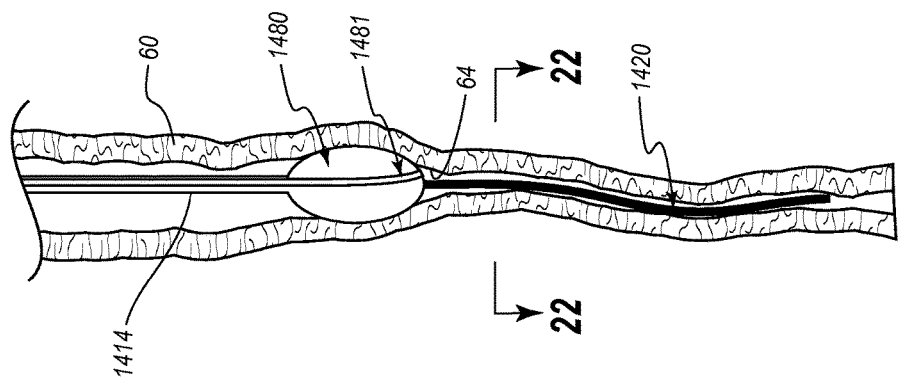
FIG. 21C is another cross-sectional view of the portion of the heat sensing system of FIG. 21A showing the esophagus collapsed into contact and/or close proximity to the heat sensor.
Figure 21B:
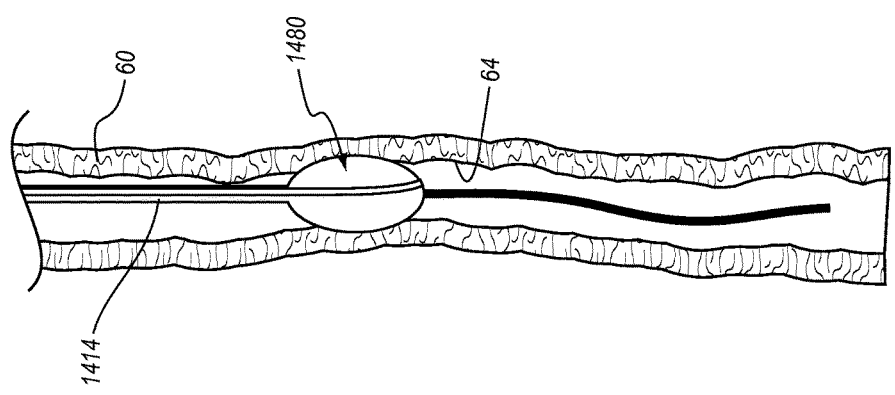
FIG. 21B is another cross-sectional view of the portion of the heat sensing system of FIG. 21A showing a balloon inflated into contact with the inner surface of the esophagus.
Figure 21A:
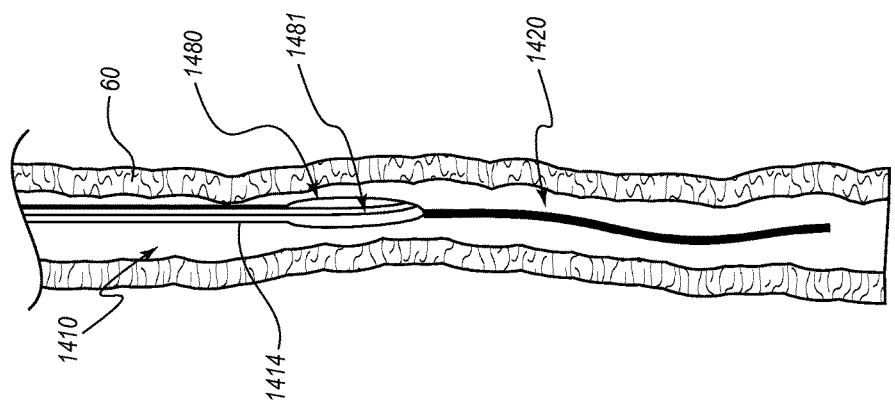
FIG. 21A is a cross-sectional view of another embodiment of a portion of a heat sensing system that includes a heat sensor that is positioned within the esophagus of a patient, wherein the heat sensing system includes an esophagus collapsing feature.
Figure 22:
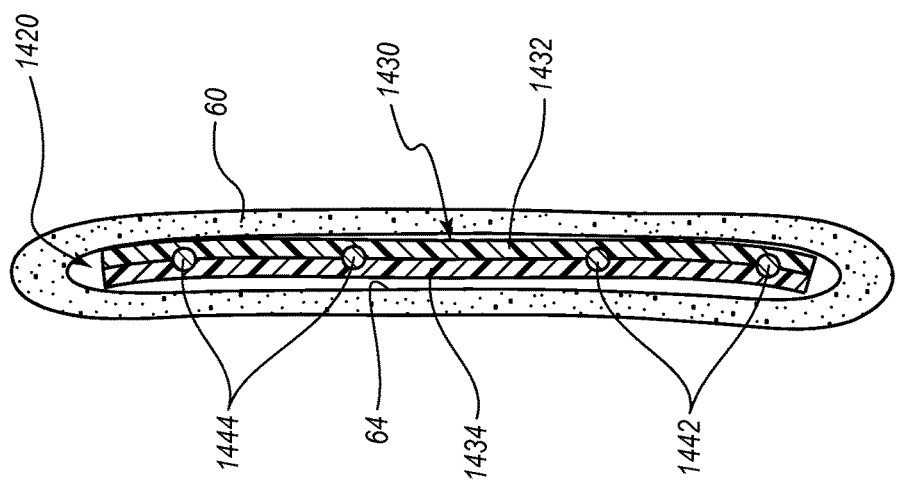
FIG. 22 is a cross-sectional view of the esophagus collapsed into contact and/or close proximity to the heat sensor taken along the view line 22-22 in FIG. 21C.

FIGS. 21A-21C and 22 illustrate another embodiment of a distal portion of a heat sensing assembly 1410, which can be used with any suitable heat sensing system described herein. The heat sensing assembly 1410 is shown within the esophagus 60 of a patient at different stages of deployment. The heat sensing assembly 1410 includes a heat sensor 1420 of any suitable variety, including any of the heat sensors disclosed herein. In the illustrated embodiment, the heat sensor 1420 particularly resembles, or may be the same as, the heat sensor 520 described above with respect to FIGS. 14-17C. As further discussed hereafter, in some arrangements, the heat sensor 1420 may include a support structure 1430 that may define a substantially planar or flat configuration when deployed within the esophagus, rather than being curled into a generally tubular shape so as to expand into close proximity to the esophageal wall in manners such as described above with respect to the heat sensor 520. Accordingly, in some embodiments, the support structure 1430 may be thicker and/or less pliable (e.g., more rigid) than the curled support structures of certain embodiments of the heat sensor 520. In other embodiments, the support structure 1430 may be pliable in manners such as discussed above, and may readily comply with, conform to, or track a shape of the esophagus. As shown in FIG. 22, in the illustrated embodiment, the support structure 1430 includes two layers 1432, 1434 that are joined together so as to encapsulate two wires 1442, 1444.

The heat sensing assembly 1410 can include any suitable device or system for collapsing the esophagus about the heat sensor 1420. Collapsing the esophagus 60 so as to bring the inner wall 64 into close contact and/or close proximity with the heat sensor 1420 can increase thermal transfer between the wall and the heat sensor 1420. In some instances, collapsing the esophagus 60 may space the esophageal wall further from the heart, which may also reduce heating of the wall during an ablation procedure. Such an arrangement may, in some instances, facilitate construction of the heat sensor 1420, given that a larger range of pliability or rigidity may be suitable for the support structure 1430 as compared with some other arrangements, as previously discussed. Such a system may be described as being configured to collapse the esophagus into contact or close proximity to the heat sensor 1420, rather than expanding or otherwise deploying the heat sensor 1420 into contact or close proximity to the esophagus.

In the illustrated embodiment, the device for collapsing the esophagus comprises an inflatable balloon 1480 having an evacuation lumen 1481. A proximal portion of the evacuation lumen 1481 is housed in a catheter 1414. Although the evacuation lumen 1481 is shown extending through the inflatable balloon 1480 in the illustrated embodiment, the evacuation lumen 1481 can be separate from the balloon 1480 in other embodiments. In some embodiments, the catheter 1414 further includes a fluid path (not shown), such as the fluid path 313 discussed above, through which an inflation fluid can be delivered to and removed from the balloon 1480. In further embodiments, the catheter 1414, or a separate catheter, can house electrical leads to and from the heat sensor 1420 and/or one or more additional fluid paths or fluid conduits to and from the heat sensor 1420, depending on the type of heat sensor. In the illustrated embodiment, the catheter 1414 houses four electrical leads (not shown), consisting of two electrical leads for each of the resistive wires 1442, 1444.

As shown in FIG. 21A, the heat sensing assembly 1410 can be introduced into the esophagus 60 with the balloon 1480 in a collapsed state. Once the heat sensor 1420 is in a desired position, inflation fluid may be used to expand the balloon 1480 into contact with the inner wall 64 of the esophagus 60, as shown in FIG. 21B. The contact may provide a fluid-tight seal. As shown in FIG. 21C, air and/or fluids about heat sensor 1420 can be evacuated via the evacuation lumen 1481 to bring the esophagus into contact and/or close proximity to the heat sensor 1420. In the illustrated embodiment, a single balloon 1480 is used in the evacuation/collapsing procedure, and the balloon 1480 is positioned proximally relative to the heat sensor 1420. In other embodiments, the balloon 1480 may be positioned distally relative to the heat sensor 1420. In still other embodiments, the heat sensing assembly 1410 may include two balloons that are positioned proximally and distally relative to the heat sensor 1420. In such embodiments, the portion of the esophagus that is between the expanded balloons can be evacuated.

In various embodiments, the heat sensor 1420 may resemble, or be the same as, other heat sensors described herein. For example, the heat sensor 1420 may resemble any of the heat sensors 120, 420, 520, 620, 720 described above and/or any of the heat sensors 1520, 1520', 1620, 1720, 1820, 1920 described below. The heat sensing assembly 1410 can include any such heat sensor and one or more esophageal collapsing mechanisms, such as the balloon 1480. Additionally, the catheter 1414 and/or one or more additional catheters can accommodate additional wire leads and/or fluid paths, depending on the type of heat sensor that is used. For example, for heat sensors such as the heat sensor 1620 discussed below, the catheter 1414 can house, in addition to the four electrical leads discussed above, two fluid conduits through which heat transfer fluid can be cycled through the heat sensor.

FIGS. 23 through 25B depict another embodiment of a heat sensor 1520 that is compatible with various heat sensing systems disclosed herein. In some embodiments, the heat sensor 1520 may be positioned along the distal end of a catheter 1514. The heat sensor 1520 can be configured to readily conform to the inner wall of the esophagus. For example, the heat sensor 1520 can be extremely compliant, or stated otherwise, can have very little rigidity. In the illustrated embodiment, the heat sensor 1520 comprises a tube 1533 having a structural integrity resembling a thread, a string, or wet noodle. That is, the tube 1533 can be readily moved into any desired orientation, and in some embodiments, may not have a significant intrinsic orientation bias. For example, the tube 1533 may readily respond to external forces (e.g., gravity, surface tension, adhesion forces) without internally counteracting those forces.

Figure 25A:
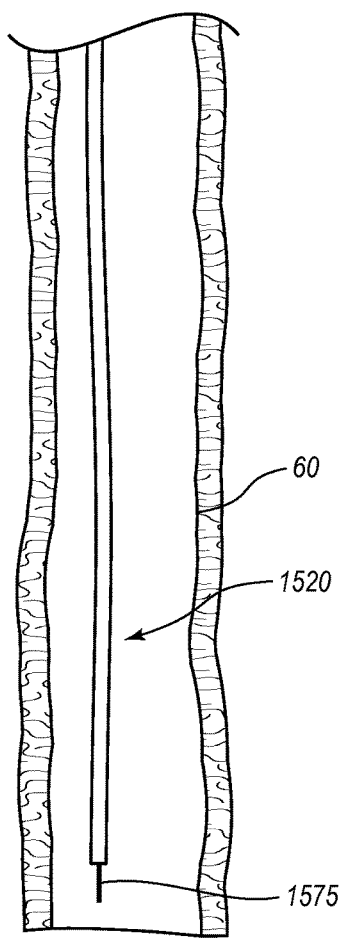
FIG. 25A is an elevation view of the heat sensor of FIG. 23 being introduced into the esophagus of a patient.
Figure 25B:
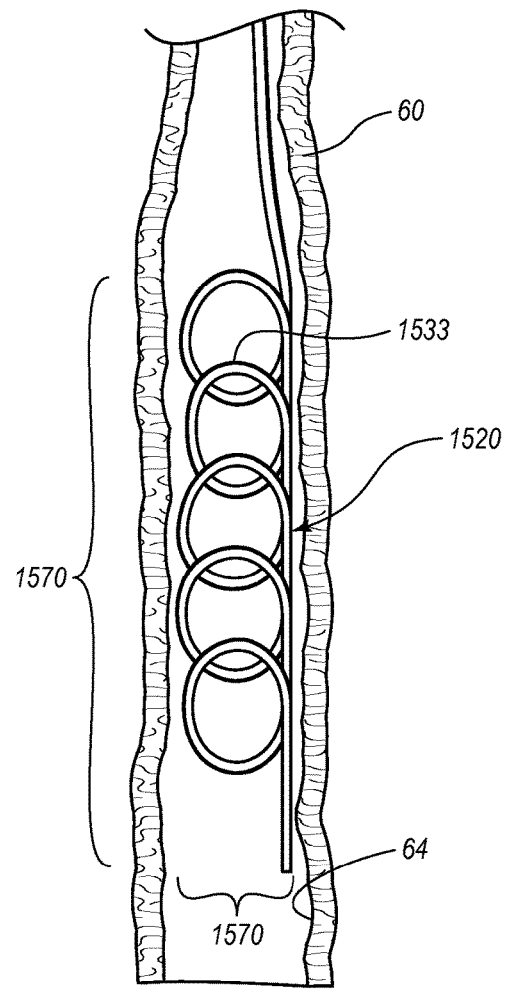
FIG. 25B is another elevation view of a later stage of the heat sensor of FIG. 23 being positioned within the esophagus of the patient.

With reference to FIG. 25A, in some embodiments, the heat sensor 1520 has an outer diameter and outer perimeter that are significantly smaller (e.g., smaller by a factor of no less than 5 times) than the inner diameter and inner perimeter of the esophagus. The heat sensor 1520 can be introduced into the esophagus 60 of a patient over a guide wire 1575. The guidewire 1575 may substantially define a straight line during the positioning stages. As shown in FIG. 25B, the guidewire 1575 may be retracted from the tube 1533. As the guidewire 1575 is retracted, a distal tip of the guidewire 1575 may trace out a generally spiral pattern relative to the esophageal wall 64. As the distal tip of the guidewire 1575 is further retracted in the proximal direction, segments of the tube 1533 can successively adhere and conform to the esophageal wall 64, such as by surface tension. When the guidewire 1575 is fully retracted from the heat sensor 1520, the tube 1533 can define a heat sensing region 1570 that extends along a longitudinal length of the esophagus 60 and extends along an inner periphery of the esophagus 60. In some arrangements, a practitioner can control a density of the tube 1533 within the heat sensing region 1570. For example, in some instances where greater sensitivity within the heat sensing region 1570 may be desired for a given tube 1533, the tube 1533 may be spiraled tightly such that adjacent loops are relatively close together. In other instances where less sensitivity within the heat sensing region 1570 may be sufficient for the same tube 1533, the tube 1533 may have a looser spiral, such that adjacent loops are further apart.

In other embodiments, the tube 1533 may be applied to the esophageal wall 64 in any suitable arrangement. For example, rather than a regular helical shape, such as shown in FIG. 25B, the tube 1533 may be applied in any other regular pattern, such as, for example, a serpentine pattern. In still other embodiments, an irregular shape or pattern may be used. For example, the tube 1533 may be permitted to assume a jumbled or squiggled shape that covers a swath of the inner esophageal wall 64. In various embodiments, the tube 1533 may be situated within the esophagus so as to extend circumferentially around no less than about ¼, ⅓, ½, ⅔, or ¾ of, or no less than a majority of, an inner perimeter of the esophagus.

As shown in FIGS. 24A and 24B, the tube 1533 can comprise a support structure 1530 that carries a heat sensing structure 1540. In the illustrated embodiment, the support structure 1530 comprises a substantially cylindrical outer layer 1532 and a substantially cylindrical inner layer 1534 that are concentric. The heat sensing structure 1540 is a single resistance wire 1542 that is laminated between the inner and outer layers 1534, 1532. The wire 1542 may be of any suitable variety, such as those discussed above, and can increase in resistance when heated. In other embodiments, more wires may be used. In other or further embodiments, the heat sensing structure 1540 can include fluid channels instead of or in addition to the heat sensing wire 1542. In the illustrated embodiment, the wire 1542 extends distally at one side of the tube 1533 along substantially the full length of the tube 1533. As shown in FIG. 24B, the wire 1542 is doubled back between the inner and outer layers 1534, 1532 at the distal end of the tube 1533, and then extends proximally at an opposite side of the tube 1533 along substantially the full length of the tube 1533. Other arrangements are also contemplated.

With continued reference to FIGS. 24A and 24B, the inner layer 1534 of the support structure 1530 can define a lumen 1585 through which the guidewire 1575 can pass. In some embodiments, the lumen 1585 is only used with the guidewire 1575. However, in other embodiments, the lumen 1585 may additionally or alternatively be used to transport heat transfer fluid (such as the heat transfer fluid 1661 discussed below with respect to FIG. 28). A heat transfer structure 1505 thus may include the lumen 1585. In the illustrated embodiment, the heat transfer fluid (such as the heat transfer fluid 1661) can flow through the lumen 1585 and drain into the esophagus 60 at the distal end of the lumen 1585.

As previously mentioned, in some embodiments, the support structure 1530 can be configured to readily conform to the inner wall of the esophagus. For example, the support structure 1530 can be elongated in a longitudinal direction, or along a longitudinal axis, and can be extremely flexible or compliant in any direction that is transverse to the longitudinal axis. However, in some embodiments, it may be desirable for the elongated support structure 1530 to be relatively or substantially inextensible along the longitudinal axis. Such an arrangement may be desirable, for example, where the trace wire 1542 is thin, fragile, and/or otherwise susceptible to breakage. In such instances, elongation of the support structure 1530 could result in breakage of the trace wire 1542, in the illustrated embodiment, or one or more trace wires 1542 in embodiments that include multiple trace wires. Such breakage would reduce the sensitivity of the heat sensor 1520 or render it inoperable. In various embodiments, the support structure 1530 has a modulus of elasticity that is sufficiently high to prevent significant elongation in the longitudinal direction. For example, in some embodiments, the modulus of elasticity is greater than that of polypropylene.

Figure 26A:
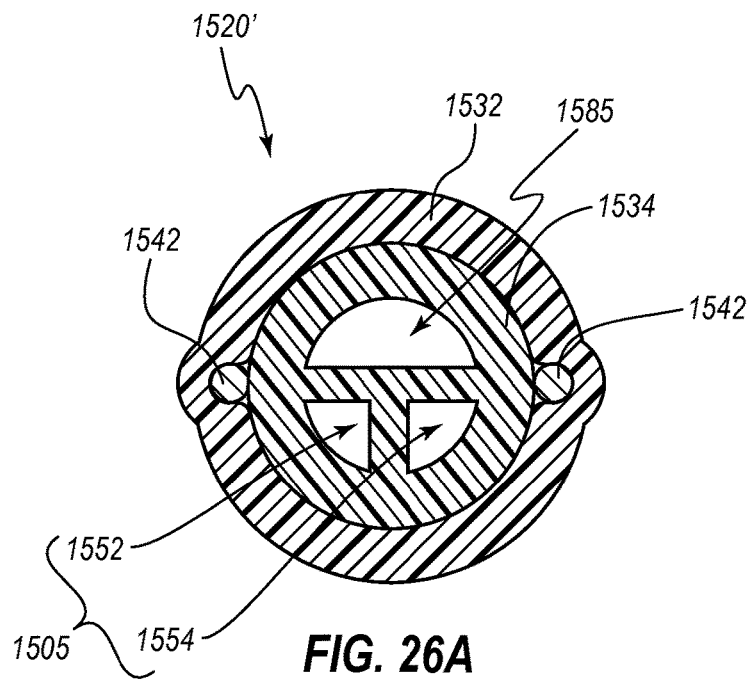
FIG. 26A is a cross-sectional view of another embodiment of a heat sensor that is similar to the heat sensor of FIG. 23, wherein the cross-sectional view is taken along a view line such as the view line 24A-24A in FIG. 23.
Figure 26B:
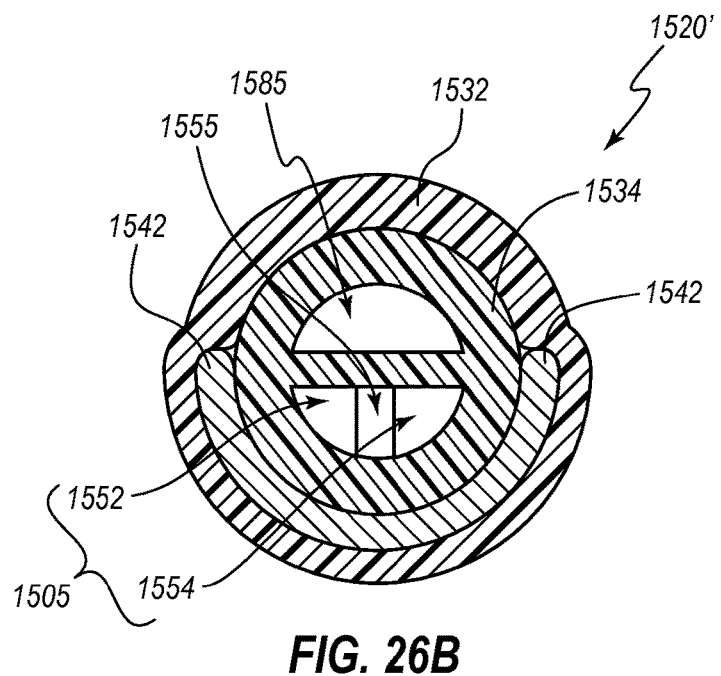
FIG. 26B is another cross-sectional view of the heat sensor of FIG. 26A, wherein the cross-sectional view is taken along a view line such as the view line 24B-24B in FIG. 23.

FIGS. 26A and 26B illustrate another embodiment of a heat sensor 1520' that is similar to the heat sensor 1520, except that the heat sensor 1520' is configured to cool the esophagus without draining the heat transfer fluid (e.g., the heat transfer fluid 1661) into the esophagus. Stated otherwise, the heat sensor 1520' includes a closed-loop heat transfer structure 1505.

The heat sensor 1520', when viewed in perspective, can closely resemble the heat sensor 1520 that is depicted in FIG. 23, except that the opening at the distal end of the tube is smaller and is shaped as a semicircle. The distal opening of the heat sensor 1520' corresponds to the distal end of the guidewire lumen 1585 that is depicted in FIGS. 26A and 26B. The guidewire lumen 1585 can extend from the proximal end to the distal end of the heat sensor 1520' such that the guidewire 1575 can extend fully through the heat sensor 1520'.

The heat sensor 1520' can include a heat transfer structure 1505, which can include two heat transfer lumens 1552, 1554. The heat transfer lumens 1552, 1554 can extend from the proximal end of the heat sensor 1520' to a position that is near, but proximal to, the distal end of the heat sensor 1520'. The lumens 1552, 1554 can be in fluid communication with each other at this distal position, as shown in FIG. 26B, but can be separate from each other along the remainder of the length of the heat sensor 1520', as shown in FIG. 26A. The distal ends of the lumens 1552, 1554 can be capped, such that only a small channel 1555 between the distal ends of the lumens 1552, 1554 provides the fluid communication between the two lumens 1552, 1554. Accordingly, in some embodiments, the heat transfer fluid (e.g., the heat transfer fluid 1661) can travel distally through the lumen 1552, and can return in a proximal direction through the lumen 1554.

Like the heat sensor 1520, the heat sensor 1520' can further include a wire 1542. Accordingly, each heat sensor 1520, 1520' can be included in a system that is configured for both heat sensing and heat transfer. For example, where the heat sensors 1520, 1520' are used in ablation procedures that tend to heat the esophagus, the heat sensors 1520, 1520' can sense heating of the esophageal wall via the wire 1542. The heat sensors 1520, 1520' can also cool the esophageal wall so as to reduce or prevent damage thereto by channeling heat transfer fluid through their respective heat transfer structures 1505 (i.e., the lumen 1585 for the heat sensor 1520 or the lumens 1552, 1554 for the heat sensor 1520'). Systems and methods in which the heat sensors 1520, 1520' can be used are discussed more fully below with respect to FIG. 28.

Figure 27A:
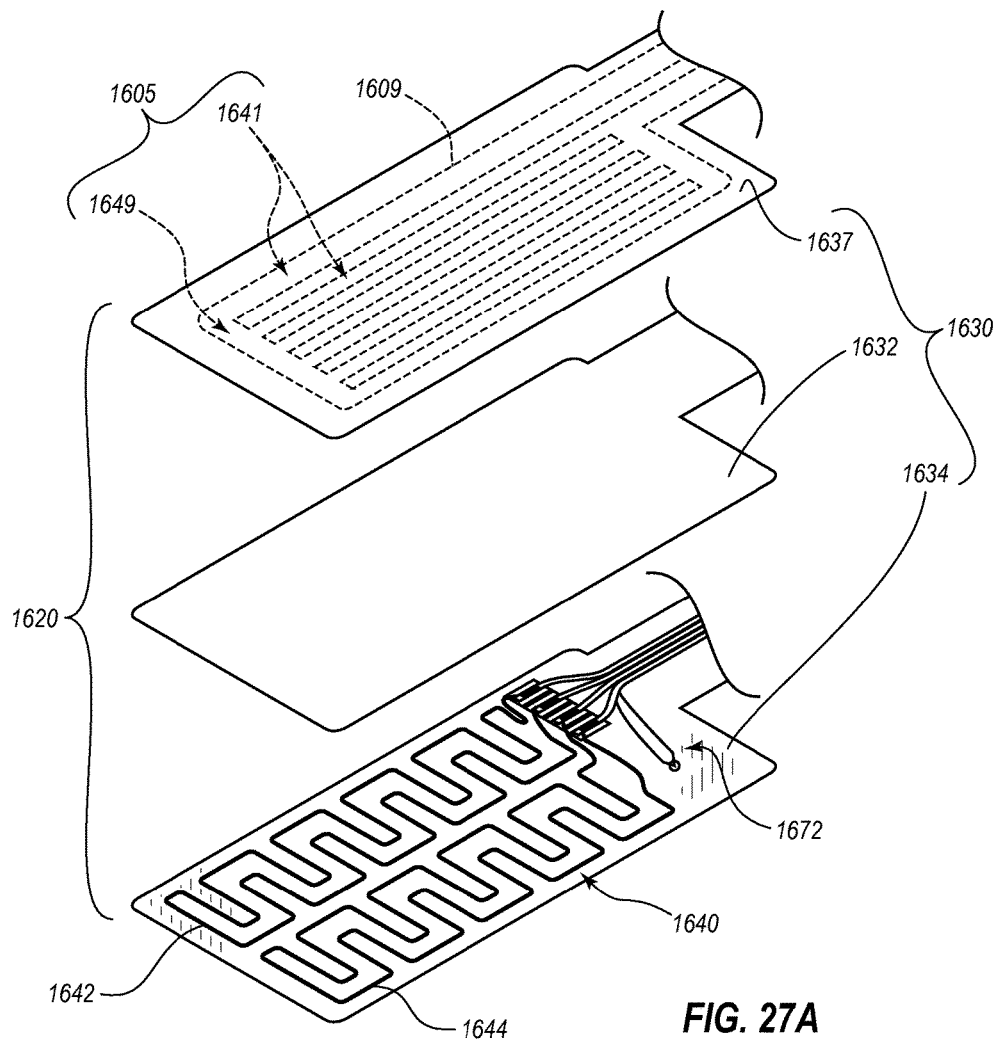
FIG. 27A is an exploded perspective view of another embodiment of a heat sensor.
Figure 27B:
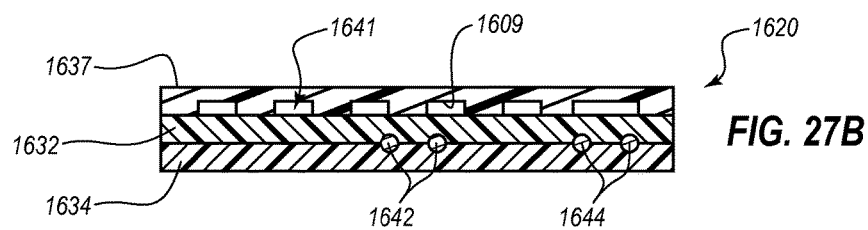
FIG. 27B is a cross-sectional view of the heat sensor of FIG. 27A.
Figure 28:
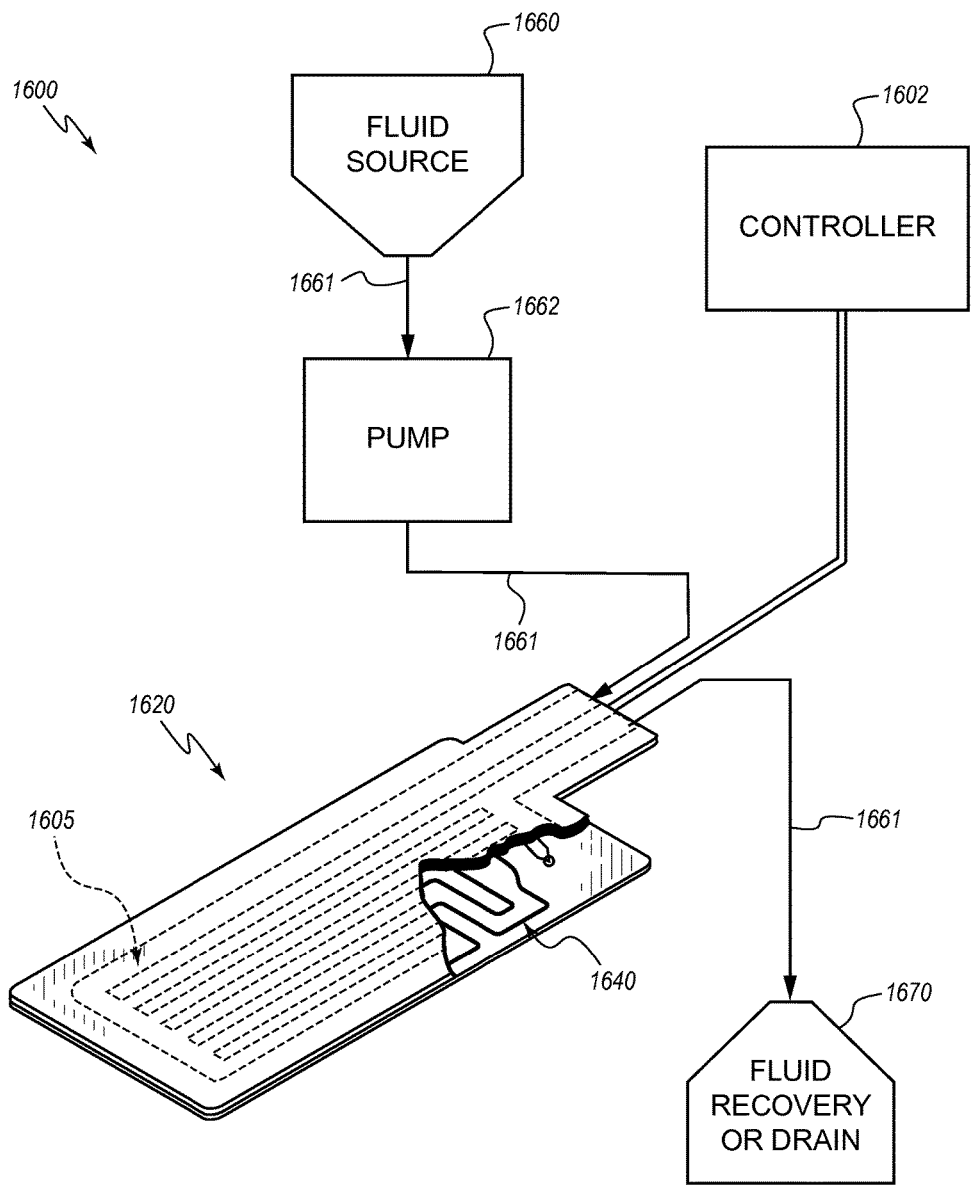
FIG. 28 is a schematic view of an embodiment of a heat sensing system that can include the heat sensor of FIG. 27A.

FIGS. 27A-28 depict another embodiment of a heat sensor 1620. Like the heat sensors 1520, 1520', the heat sensor 1520 can include both a heat sensing structure 1640 and a heat transfer circuit or heat transfer structure 1605. As a further similarity, the heat sensing structure 1640 includes wires 1642, 1644 from which changes in resistive properties can be detected, whereas the heat transfer structure 1605 is configured to channel a heat transfer fluid along a fluid circuit or fluid path (e.g., a series of interconnected conduits). The heat sensor 1620 thus may be said to include an active heat transfer (e.g., cooling) circuit.

The heat sensor 1620 comprises a support structure 1630. In the illustrated embodiment, the support structure 1630 comprises a laminate of three layers 1632, 1634, 1637 of material. The layers 1632, 1634, 1637 may be of any suitable material, such as those discussed above with respect to the support structure 130. The layer 1634 may also be referred to as a substrate, the layer 1632 may also be referred to as a superstrate, and the layer 1637 may also be referred to as a heat transfer layer.

In the illustrated embodiment, the heat sensor 1620 resembles the heat sensor 520 described above with respect to FIGS. 14-17C. Moreover, that portion of the heat sensor 1620 that closely resembles the heat sensor 520 can operate in the same manners as the heat sensor 520 described above. However, in addition to a laminate structure defined by the layers 1632, 1634 that encapsulates the resistive wires 1642, 1644 and a thermocouple 1672, the heat sensor 1620 includes the further layer 1637, which at least partially defines the heat transfer structure 1605. In particular, the lamination layer 1637 includes a series of grooves 1609 that cooperate with the middle layer 1632 to define fluid channels 1641, 1649 through which heat transfer fluid 1661 can be cycled.

As shown in FIG. 28, the heat sensor 1620 can be used in a heat sensing and heat transferring system 1600, which can include a controller 1602, a fluid source 1660, a pump 1662, and a fluid recovery receptacle 1670. In some embodiments, the controller 1602 can be in electrical or other communication with the pump 1662 so as to control operation of the pump 1662. For example, the controller 1602 may adjust a speed of the pump 1662. In other embodiments, the pump 1662 may be operated independently of the controller 1602 (e.g., may be operated manually). In other embodiments, the pump 1662 may not be used, such as when the fluid source 1660 comprises pressurized fluid (e.g., pressurized air). The controller 1602 can resemble the controller 102 discussed above, and may be capable of carrying out methods and processes discussed above and hereafter. For example, the controller 1602 may include hardware and/or software that is programmed, or programmable, to control one or more of the components of the heat sensing system 1600 to carry out various processes. Communicative connections between the controller 1602 and the various components of the heat sensing system 1600 are not shown in FIG. 28.

The fluid source 1660 can provide a supply of heat transfer fluid 1661. The heat transfer fluid 1661 can comprise any suitable fluid. It may be desirable for the heat transfer fluid 1661 to be non-toxic or otherwise suitable for ingestion by a patient in the event of a leak or where the heat transfer fluid 1661 is drained into the esophagus of the patient. However, in some embodiments, it may be most desirable for the heat transfer fluid 1661 to have particular heating characteristics, such as a desired specific heat, and precautions may be made where such fluids may potentially harmful if ingested. In some embodiments, the recovered heat transfer fluid 1661 is cycled from the fluid recovery receptacle 1670 back to the fluid source 1660. For example, in some embodiments, these components may comprise a common fluid reservoir.

The pump 1662 can move heat transfer fluid 1661 through the heat sensing system 1600. In particular, in the illustrated embodiment, the pump 1662 moves heat transfer fluid 1661 from the fluid source 1660, through the heat sensor 1620, and to the fluid recovery receptacle 1670. Any suitable fluid connections between the various components of the heat sensing system 1600 are possible, and are schematically represented by arrows that show the direction of fluid flow.

In other embodiments, rather than having a fluid recovery receptacle 1670, the heat transfer fluid 1661 may instead be drained after it exits the heat sensor 1620. In certain of such embodiments, used heat transfer fluid 1661 may drain into the esophagus and may proceed to the patient's stomach. In certain of such embodiments, the heat transfer fluid 1661 may comprise water, air, saline solution, or some other ingestible fluid. In other embodiments the used heat transfer fluid 1661 may be drained or vented at an exterior of the patient. For example, when the heat transfer fluid 1661 comprises compressed air, the used air may be vented to a surrounding environment or atmosphere after it has passed through the system 1600.

One or more catheters, such as those described above, may be used to couple the heat sensor 1620 with the heat transfer fluid circuit and/or the controller 1602. For example, the one or more catheters may include lumens or fluid paths for conducting the heat transfer fluid 1661 to and from the heat sensor 1620 and/or they may include electrical leads that extend between the heat sensor 1620 and the controller 1602.

In operation, the controller 1602 can determine when the resistance of one or more of the wires 1642, 1644 increases (or decreases, as in cryoablation) by an amount that merits the signaling of a warning (e.g., to a practitioner) and/or the automatic termination of the ablation procedure. The pump 1662 can draw heat transfer fluid 1661 from the fluid source 1660 and urge the heat transfer fluid 1661 through the heat transfer structure 1605 of the heat sensor 1620 and into the fluid recovery receptacle 1670. In some arrangements, the pump 1662 establishes at a steady flow rate. In certain of such arrangements, the controller 1602 determines that equilibrium is reached before ablation commences. For example, the controller 1602 may determine that the resistance in the wires 1642, 1644 has reached a constant value after the heat transfer fluid 1661 has coursed through the heat transfer structure 1605 for a sufficient time to have cooled the esophageal wall to a steady temperature. Accordingly, in some embodiments, the heat sensor 1620 is capable of reducing or preventing damage to the esophagus by simultaneously sensing heating of the esophagus so as to terminate an ablation procedure before damage is done and cooling the esophagus to reduce the risk of burning from the outset.

In some embodiments, the heat sensor 1620 is configured to curl in a manner similar to the heat sensor 520, as depicted in and described with respect to FIGS. 17A-17C, and can conform to and/or track natural movements of the esophagus. In other embodiments, the heat sensor 1620 may be deployed into a substantially flat state and the esophagus may be collapsed about the heat sensor 1620 in any suitable manner, such as that described above with respect to FIGS. 21A-30. In some embodiments, the outer layer 1634 of the support structure 1630, which is in contact with the resistive wires 1642, 1644, may be positioned closest to the ablation site.

Figure 29B:
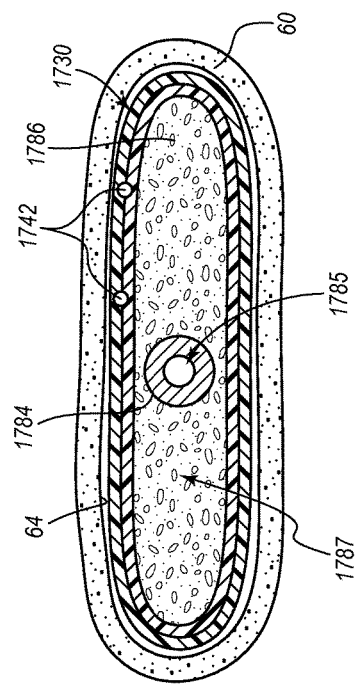
FIG. 29B is a cross-sectional view of the deployed heat sensor of FIG. 29A taken along the view line 29B-29B in FIG. 29A.
Figure 29C:
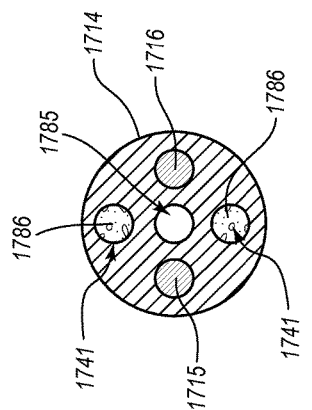
FIG. 29C is another cross-sectional view of the deployed heat sensor of FIG. 29A taken along the view line 29C-29C in FIG. 29A.
Figure 29A:
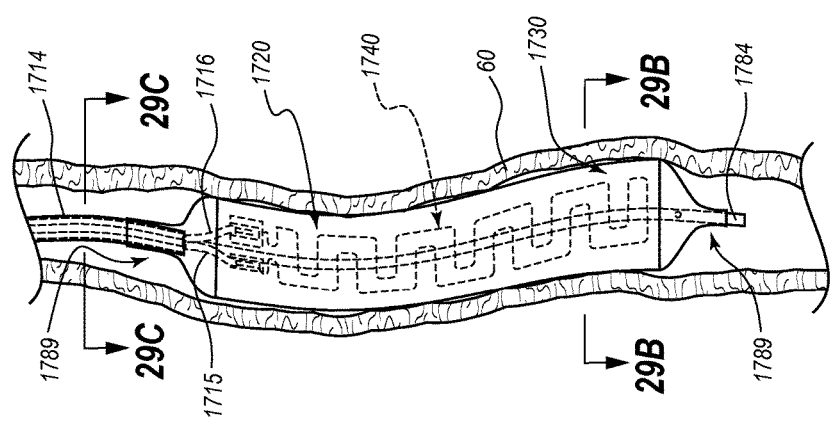
FIG. 29A is an elevation view of another embodiment of a heat sensor that is positioned within the esophagus of a patient.

FIGS. 29A-29C illustrate another embodiment of a heat sensor 1720 which can be used in any suitable heat sensing and heat transferring system, such as the system 1600 (with modifications, as discussed below). The heat sensor 1720 can closely resemble the heat sensor 420 discussed above, and can include a similar support structure 1730 and heat sensing structure 1740. In particular, the heat sensing structure 1740 can include one or more resistive wires 1742. In the illustrated embodiment, a single resistive wire 1742 is used, which extends about a full periphery of an inner layer of the support structure 1730 to form a twin helical pattern, as schematically shown in FIG. 29A. Other patterns or configurations are possible. The wire 1742 is electrically connected to electrical leads 1715, 1716 at either end thereof.

The heat sensor 1720 can be positioned at the end of a catheter 1714, which can include the electrical leads 1715, 1716 and fluid channels 1741. The heat sensor can include a wire sheath 1784 that defines a lumen 1785 through which a guidwire can extend. The catheter 1714 can define a proximal portion of the lumen 1785. The support structure 1730 and the wire sheath 1784 can cooperate to define an inflatable cavity 1787.

An inflation fluid 1786 can be introduced into the inflatable cavity 1787 to expand the support structure 1730 into contact with and/or close proximity to the inner wall 64 of the esophagus 60 in manners such as described above with respect to FIGS. 12A-12C. Accordingly, FIG. 29B may, in some instances, resemble an deployment stage such as that depicted in FIG. 12C, and the heat sensor 1720 may be in a conformance, tracking, following, or according state in which the heat sensor 1720 conforms to the natural shape of the esophagus substantially without displacing the esophagus. In some embodiments, the inflation fluid 1786 can comprise a heat transfer fluid such as described above, which may be configured to counteract the effects of an ablation procedure on the esophageal wall. For example, the inflation fluid 1786 can be cooled for heat-producing ablation procedures (or it may be heated for cryoablation). The inflation fluid 1786 may be circulated through the inflatable cavity 1787 during the ablation procedure so as to assist with heat exchange. For example, the inflation fluid 1786 may be continuously supplied to the cavity 1787 via one fluid conduit 1741 of the catheter 1714 and continuously drained from the cavity 1787 via the other fluid conduit 1741 of the catheter 1714. In some embodiments, the heat sensing and heat transfer system in which the heat sensor 1720 operates includes a controller, which may monitor the pressure of the inflation fluid 1786 and, in some arrangements, maintain the pressure at a substantially constant value during an ablation procedure.

Figure 30A:
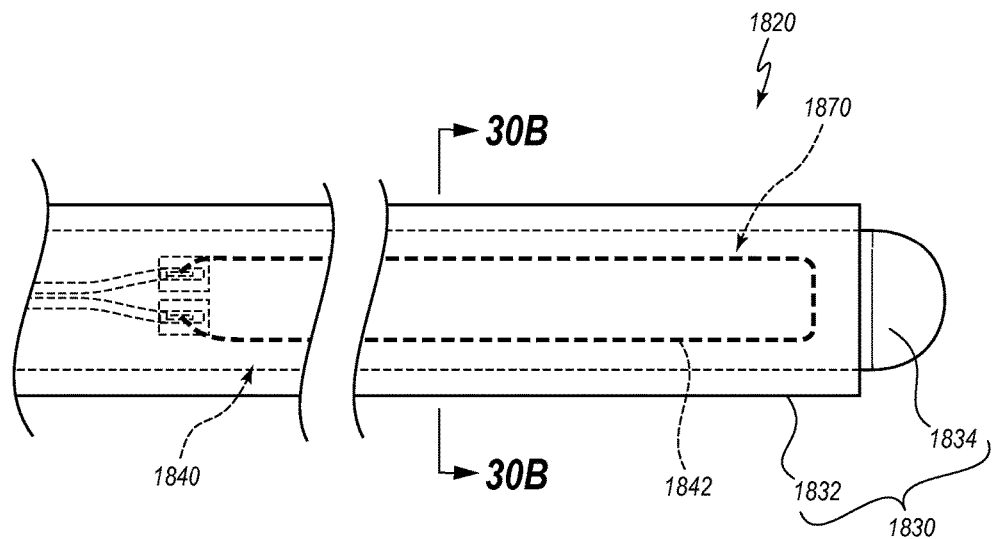
FIG. 30A is a partial side elevation view of another embodiment of a heat sensor.
Figure 30B:
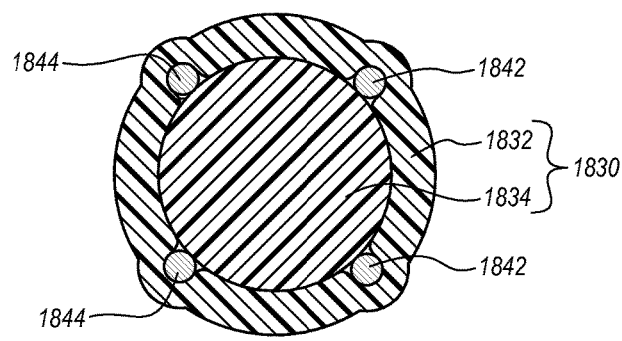
FIG. 30B is a cross-sectional view of the heat sensor of FIG. 30A taken along the view line 30B-30B of FIG. 30A.

FIGS. 30A and 30B depict another embodiment of a heat sensor 1820 that is compatible with various heat sensing systems described herein. The heat sensor 1820 includes a support structure 1830 to which a heat sensing structure 1840 is mounted. In the illustrated embodiment, the support structure 1830 includes a core 1834 and a sleeve 1832 that are affixed to each other, such as by heat shrinking, lamination, or any other suitable method. The core 1834 may be solid and/or flexible in at least one direction that is transverse to a longitudinal axis of the heat sensor 1820. The sleeve 1832 encapsulates the heat sensing structure 1840, which includes two resistive wires 1842, 1844. Any other suitable number and arrangement of the wires is contemplated. In the illustrated embodiment, two branches of each wire 1842, 1844 extend in straight lines that are parallel to a longitudinal axis of the heat sensor 1820. The wire branches are angularly spaced about the core 1834 and are angularly offset from each adjacent branch by about 90 degrees. Such a symmetrical arrangement can aid in sensing heating near the sensor 1820, regardless of the rotational orientation of the sensor.

The heat sensing structure 1840 defines a heat sensing region 1870 that is coextensive with the wires 1842, 1844. In some embodiments, a sensitivity of the heat sensing region 1870 may be increased by using additional wires. For example. a greater density of wires (e.g., with angular offsets between adjacent wires of no greater than about 15, 30, 45, 60, or 75 degrees) can provide a more noticeable and/or quicker response of the heat sensor 1840, as it can ensure that one or more wire branches will be close to region of the esophagus that is being heated, regardless of the angular orientation of the heat sensor 1840 within the esophagus.

Figure 31A:
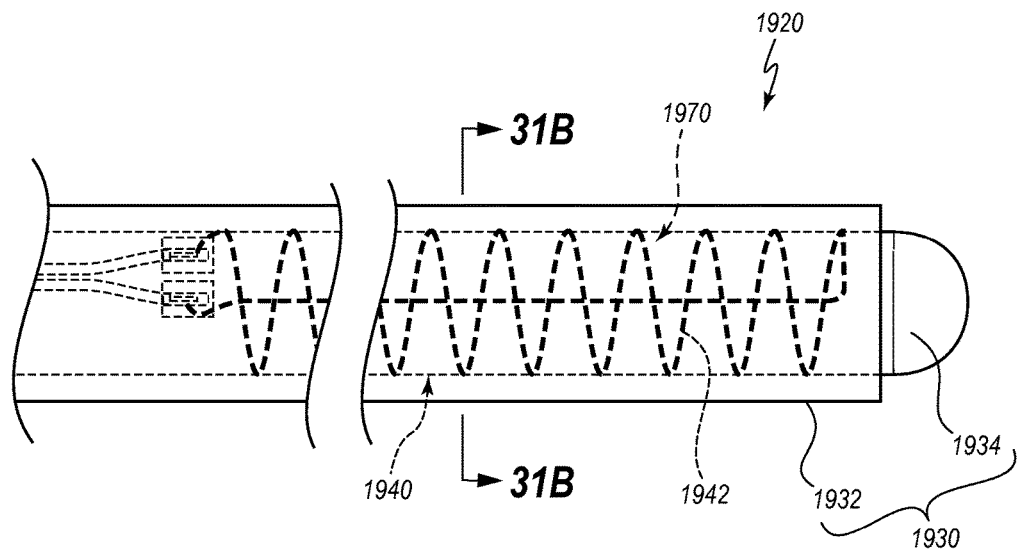
FIG. 31A is a partial side elevation view of another embodiment of a heat sensor.
Figure 31B:
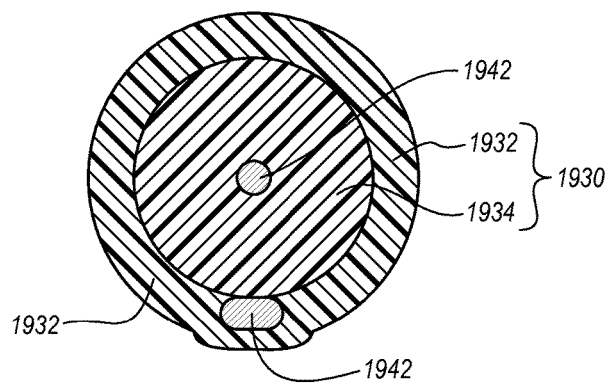
FIG. 31B is a cross-sectional view of the heat sensor of FIG. 31A taken along the view line 31B-31B of FIG. 31A.

FIGS. 31A and 31B depict another embodiment of a heat sensor 1920 that resembles the heat sensor 1820 and is compatible with various heat sensing systems described herein. The heat sensor 1920 also includes a support structure 1930 having a core 1934 and a sleeve 1932 within which a heat sensing structure 1940 is encapsulated. However, in the illustrated embodiment, the heat sensing structure 1940 includes a single resistive wire 1942. The heat sensing structure 1940 can provide a heat sensing region 1970 that can have the same dimensions (e.g., length, width, girth, etc.) as the heat sensing region 1870 discussed above. However, due to the configuration of the wire 1942, the heat sensing region 1970 may be more sensitive. For example, in the illustrated embodiment, the wire 1942 includes a first branch that is substantially collinear with a longitudinal axis of the heat sensor 1920. However, a second branch of the wire 1942 is wound about the core 1932 in a relatively tight helix. The second branch thus provides a greater "wire density" within the heat sensing region 1970 than is present in the heat sensing region 1870 depicted in FIG. 38A. The generally symmetrical arrangement of the wire 1942 can permit the heat sensor 1920 to have a relatively consistent sensitivity to heating, regardless of a rotational orientation of the heat sensor 1920.

As with the heat sensors 1520, 1520' discussed above, in some embodiments, the support structures 1830, 1930 are flexible in at least a first direction that is transverse to a longitudinal direction of the heat sensor in at least the heat sensing region 1870, 1970. However, in further embodiments, the support structures 1830, 1930 can be substantially inextensible in the longitudinal direction. Such longitudinal stiffness can protect the wires 1842, 942 from damage that may be caused by pulling forces in the longitudinal direction. Such properties of the support structures 1830, 1930 can permit the heat sensors 1820, 1920 to be purposefully shaped during insertion into the esophagus and/or can allow the heat sensor to conform to the shape of the esophagus (e.g., a specific contour of the anatomy).

As previously mentioned, while the drawings and written description have focused on illustrative devices, systems, and methods related to AF ablation procedures, it is to be understood that embodiments may be used in any other suitable context. Moreover, it will be understood by those having skill in the art that changes may be made to the details of the above-described embodiments without departing from the underlying principles presented herein. For example, any suitable combination of various embodiments, or the features thereof, is contemplated.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified.

References to approximations are made throughout this specification, such as by use of the terms "about" or "approximately." For each such reference, it is to be understood that, in some embodiments, the value, feature, or characteristic may be specified without approximation. For example, where qualifiers such as "about," "substantially," and "generally" are used, these terms include within their scope the qualified words in the absence of their qualifiers. For example, where the term "substantially planar" is recited with respect to a feature, it is understood that in further embodiments, the feature can have a precisely planar orientation.

Reference throughout this specification to "an embodiment" or "the embodiment" means that a particular feature, structure or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment.

The claims following this written disclosure are hereby expressly incorporated into the present written disclosure, with each claim standing on its own as a separate embodiment. This disclosure includes all permutations of the independent claims with their dependent claims. Moreover, additional embodiments capable of derivation from the independent and dependent claims that follow are also expressly incorporated into the present written description. These additional embodiments are determined by replacing the dependency of a given dependent claim with the phrase "any of the preceding claims up to and including claim [x]," where the bracketed term "[x]" is replaced with the number of the most recently recited independent claim. For example, for the first claim set that begins with independent claim 1, claim 3 can depend from either of claims 1 and 2, with these separate dependencies yielding two distinct embodiments; claim 4 can depend from any one of claim 1, 2, or 3, with these separate dependencies yielding three distinct embodiments; claim 5 can depend from any one of claim 1, 2, 3, or 4, with these separate dependencies yielding four distinct embodiments; and so on.

Recitation in the claims of the term "first" with respect to a feature or element does not necessarily imply the existence of a second or additional such feature or element. Elements specifically recited in means-plus-function format, if any, are intended to be construed in accordance with 35 U.S.C. § 112(f). Embodiments of the invention in which an exclusive property or privilege is claimed are defined as follows:

The invention claimed is:

1. A heat sensing system comprising:
    a heat sensor that comprises:
        a heat sensing wire formed of a single continuous one-piece wire having a resistivity that varies with temperature, the heat sensing wire extending along a continuous path that defines a heat sensing region, wherein an area spanned by the heat sensing region extends along no less than ¼ of a lateral perimeter of the heat sensor at which contact with an inner wall of an anatomical vessel can be achieved when the heat sensor is deployed in the vessel;
        a first connection interface at a first end of the heat sensing wire at a first end of the continuous path;
        a second connection interface at a second end of the heat sensing wire at a second end of the continuous path, the first and second connection interfaces being the only connection interfaces in electrical contact with the heat sensing wire; and
        an encapsulation covering the heat sensing wire, the encapsulation being configured to electrically isolate the heat sensing wire from an electrically conductive substance at an interior of the anatomical vessel when the heat sensor is deployed within the vessel, and the encapsulation being configured to permit heat transfer to, from, or both to and from the heat sensing wire, wherein the encapsulation is configured to transition between a compressed state in which the encapsulation has a first cross-sectional profile and an expanded state in which the encapsulation has a second cross-sectional profile that is larder than the first cross-sectional profile, the encapsulation defining the lateral perimeter of the heat sensor, wherein the lateral perimeter is the same whether the encapsulation is in the compressed state or in the expanded state,
        wherein each of the heat sensing wire and the encapsulation is flexible to permit the heat sensing region defined by the heat sensing wire to conform to an inner surface of the anatomical vessel when the heat sensor is deployed within the anatomical vessel; and
    a controller coupled with the heat sensor, wherein the controller is configured to detect that heating of the heat sensing region at any location along the heat sensing wire has occurred due to changes to an overall electrical resistance of the heat sensing wire.

2. The heat sensing system of claim 1, wherein the first and second connection interfaces are connected to respective first and second electrical leads via which the heat sensor can be electrically coupled with the controller.

3. The heat sensing system of claim 1, wherein the heat sensor further comprises a reference temperature sensor positioned in proximity to the heat sensing region, wherein the reference temperature sensor is configured to detect a reference temperature and communicate with the controller, wherein the controller is configured to monitor the reference temperature, and wherein the controller is configured to detect that the heating of the heat sensing region at any location along the heat sensing wire has occurred by monitoring the changes to the overall electrical resistance of the heat sensing wire in relation to the reference temperature.

4. The heat sensing system of claim 1, wherein the encapsulation of the heat sensor comprises a substrate that comprises a solid core and further comprises a superstrate that comprises a tubular structure that sheaths the core.

5. The heat sensing system of claim 1, wherein the encapsulation of the heat sensor is substantially planar when in a natural state and is configured to be curled about an axis that extends in a longitudinal direction when the heat sensor is positioned within the anatomical vessel such that the encapsulation extends along at least a majority of an inner perimeter of the anatomical vessel, and wherein the longitudinal direction of the heat sensor corresponds to a longitudinal direction of the anatomical vessel when the heat sensor is deployed in the anatomical vessel.

6. The heat sensing system of claim 1, wherein the encapsulation is resiliently flexible with an intrinsic bias toward the expanded state.

7. The heat sensing system of claim 1, wherein the encapsulation is flexible, but not resiliently flexible, such that the encapsulation readily transitions between the compressed state and the expanded state, yet is intrinsically unbiased relative to each of the compressed and expanded states.

8. The heat sensing system of claim 1, wherein the encapsulation is devoid of bias toward a natural shape in each of the compressed state and the expanded state.

9. The heat sensing system of claim 1, wherein the controller is further configured to activate an alarm when a temperature is detected by the controller that reaches or exceeds a threshold value, wherein a change in the temperature is related to the overall electrical resistance of the heat sensing wire.

10. The heat sensing system of claim 1, wherein the controller is further configured to determine a rate of change of a temperature profile that is monitored by the controller, wherein the rate of change is determined by measuring the changes to the overall electrical resistance of the heat sensing wire over time.

11. The heat sensing system of claim 10, wherein the controller is configured to activate an alarm if the rate of change meets or exceeds a threshold value.

12. A heat sensing system comprising:
a heat sensor that comprises:
a heat sensing wire formed of a single continuous one-piece wire having a resistivity that varies with temperature, the heat sensing wire extending along a grid-shaped path that defines a heat sensing region;
a first electrical lead coupled to a first end of the heat sensing wire at a first junction, the first electrical lead being positioned outside the heat sensing region;
a second electrical lead coupled to a second end of the heat sensing wire at a second junction, the second electrical lead being positioned outside the heat sensing region; and
an encapsulation covering the heat sensing wire, the encapsulation being configured to electrically isolate the heat sensing wire from an electrically conductive substance at an interior of an anatomical vessel within a patient when the heat sensor is deployed within the vessel, and the encapsulation being configured to permit heat transfer to, from, or both to and from the heat sensing wire, wherein each of the encapsulation and the heat sensing wire is flexible to permit the heat sensing region defined by the heat sensing wire to conform to an inner surface of the anatomical vessel when the heat sensor is deployed within the anatomical vessel; and
a controller configured to couple with the first and second electrical leads of the heat sensor to electrically communicate with the heat sensing wire, wherein the controller is configured to detect that heating of the heat sensing region at any location along the heat sensing wire has occurred due to changes to an overall electrical resistance of the heat sensing wire.

13. The heat sensing system of claim 12, wherein the first and second electrical leads are configured to extend from an interior of the patient to an exterior of the patient when the heat sensor is deployed within the anatomical vessel.

14. The heat sensing system of claim 12, wherein the heat sensor further comprises a connector attached to the first and second electrical leads, wherein the connector is configured to be coupled with the controller at an exterior of the patient when the heat sensor is deployed within the anatomical vessel.

15. The heat sensing system of claim 12, wherein the encapsulation is configured to transition between a compressed state in which the encapsulation has a first cross-sectional profile and an expanded state in which the encapsulation has a second cross-sectional profile that is larger than the first cross-sectional profile, the encapsulation defining a lateral perimeter that is the same whether the encapsulation is in the compressed state or in the expanded state.

16. The heat sensing system of claim 12, wherein the encapsulation is resiliently flexible with an intrinsic bias toward an expanded state.

17. The heat sensing system of claim 12, wherein the encapsulation is flexible, but not resiliently flexible, such that the encapsulation readily transitions between a compressed state and an expanded state, yet is intrinsically unbiased relative to each of the compressed and expanded states.

18. The heat sensing system of claim 12, wherein the encapsulation is devoid of bias toward a natural shape in each of a compressed state and an expanded state.

19. The heat sensing system of claim 12, wherein the controller is further configured to activate an alarm when a temperature is detected by the controller that reaches or exceeds a threshold value, wherein a change in the temperature is related to the overall electrical resistance of the heat sensing wire.

20. The heat sensing system of claim 12, wherein the controller is further configured to determine a rate of change of a temperature profile that is monitored by the controller, wherein the rate of change is determined by measuring the changes to the overall electrical resistance of the heat sensing wire over time.

21. The heat sensing system of claim 20, wherein the controller is configured to activate an alarm if the rate of change meets or exceeds a threshold value.

22. A heat sensing system comprising:
a heat sensor that comprises:
a heat sensing wire formed of a single continuous one-piece wire having a resistivity that varies with temperature, the heat sensing wire extending along a continuous path that defines a heat sensing region, wherein an area spanned by the heat sensing region extends along no less than ¼ of a lateral perimeter of the heat sensor at which contact with an inner wall of an anatomical vessel can be achieved when the heat sensor is deployed in the vessel;

a first connection interface at a first end of the heat sensing wire at a first end of the continuous path;

a second connection interface at a second end of the heat sensing wire at a second end of the continuous path, the first and second connection interfaces being the only connection interfaces in electrical contact with the heat sensing wire; and an encapsulation covering the heat sensing wire, the encapsulation being configured to electrically isolate the heat sensing wire from an electrically conductive substance at an interior of the anatomical vessel when the heat sensor is deployed within the vessel, and the encapsulation being configured to permit heat transfer to, from, or both to and from the heat sensing wire, wherein the encapsulation is flexible, but not resiliently flexible, such that the encapsulation readily transitions between a compressed state and an expanded state, yet is intrinsically unbiased relative to each of the compressed and expanded states, wherein each of the heat sensing wire and the encapsulation is flexible to permit the heat sensing region defined by the heat sensing wire to conform to an inner surface of the anatomical vessel when the heat sensor is deployed within the anatomical vessel; and a controller coupled with the heat sensor, wherein the controller is configured to detect that heating of the heat sensing region at any location along the heat sensing wire has occurred due to changes to an overall electrical resistance of the heat sensing wire.

23. The heat sensing system of claim 22, wherein the first and second connection interfaces are connected to respective first and second electrical leads via which the heat sensor can be electrically coupled with the controller.

24. The heat sensing system of claim 22, wherein the heat sensor further comprises a reference temperature sensor positioned in proximity to the heat sensing region, wherein the reference temperature sensor is configured to detect a reference temperature and communicate with the controller, wherein the controller is configured to monitor the reference temperature, and wherein the controller is configured to detect that the heating of the heat sensing region at any location along the heat sensing wire has occurred by monitoring the changes to the overall electrical resistance of the heat sensing wire in relation to the reference temperature.

25. The heat sensing system of claim 22, wherein the encapsulation of the heat sensor comprises a substrate that comprises a solid core and further comprises a superstrate that comprises a tubular structure that sheaths the core.

26. The heat sensing system of claim 22, wherein the encapsulation of the heat sensor is substantially planar when in a natural state and is configured to be curled about an axis that extends in a longitudinal direction when the heat sensor is positioned within the anatomical vessel such that the encapsulation extends along at least a majority of an inner perimeter of the anatomical vessel, and wherein the longitudinal direction of the heat sensor corresponds to a longitudinal direction of the anatomical vessel when the heat sensor is deployed in the anatomical vessel.

27. The heat sensing system of claim 22, wherein the encapsulation is configured to transition between the compressed state in which the encapsulation has a first cross-sectional profile and the expanded state in which the encapsulation has a second cross-sectional profile that is larger than the first cross-sectional profile, the encapsulation defining the lateral perimeter of the heat sensor, wherein the lateral perimeter is the same whether the encapsulation is in the compressed state or in the expanded state.

28. The heat sensing system of claim 22, wherein the controller is further configured to activate an alarm when a temperature is detected by the controller that reaches or exceeds a threshold value, wherein a change in the temperature is related to the overall electrical resistance of the heat sensing wire.

29. The heat sensing system of claim 22, wherein the controller is further configured to determine a rate of change of a temperature profile that is monitored by the controller, wherein the rate of change is determined by measuring the changes to the overall electrical resistance of the heat sensing wire over time.

30. A heat sensing system comprising:
a heat sensor that comprises:
a heat sensing wire formed of a single continuous one-piece wire having a resistivity that varies with temperature, the heat sensing wire extending along a continuous path that defines a heat sensing region, wherein an area spanned by the heat sensing region extends along no less than ¼ of a lateral perimeter of the heat sensor at which contact with an inner wall of an anatomical vessel can be achieved when the heat sensor is deployed in the vessel;

a first connection interface at a first end of the heat sensing wire at a first end of the continuous path;

a second connection interface at a second end of the heat sensing wire at a second end of the continuous path, the first and second connection interfaces being the only connection interfaces in electrical contact with the heat sensing wire; and an encapsulation covering the heat sensing wire, the encapsulation being configured to electrically isolate the heat sensing wire from an electrically conductive substance at an interior of the anatomical vessel when the heat sensor is deployed within the vessel, and the encapsulation being configured to permit heat transfer to, from, or both to and from the heat sensing wire, wherein the encapsulation is devoid of bias toward a natural shape in each of a compressed state and an expanded state, wherein each of the heat sensing wire and the encapsulation is flexible to permit the heat sensing region defined by the heat sensing wire to conform to an inner surface of the anatomical vessel when the heat sensor is deployed within the anatomical vessel; and a controller coupled with the heat sensor, wherein the controller is configured to detect that heating of the heat sensing region at any location along the heat sensing wire has occurred due to changes to an overall electrical resistance of the heat sensing wire.

31. The heat sensing system of claim 30, wherein the first and second connection interfaces are connected to respective first and second electrical leads via which the heat sensor can be electrically coupled with the controller.

32. The heat sensing system of claim 30, wherein the heat sensor further comprises a reference temperature sensor positioned in proximity to the heat sensing region, wherein the reference temperature sensor is configured to detect a reference temperature and communicate with the controller, wherein the controller is configured to monitor the reference temperature, and wherein the controller is configured to detect that the heating of the heat sensing region at any location along the heat sensing wire has occurred by monitoring the changes to the overall electrical resistance of the heat sensing wire in relation to the reference temperature.

33. The heat sensing system of claim 30, wherein the encapsulation of the heat sensor comprises a substrate that comprises a solid core and further comprises a superstrate that comprises a tubular structure that sheaths the core.

34. The heat sensing system of claim 30, wherein the encapsulation of the heat sensor is substantially planar when in the natural state and is configured to be curled about an axis that extends in a longitudinal direction when the heat sensor is positioned within the anatomical vessel such that the encapsulation extends along at least a majority of an inner perimeter of the anatomical vessel, and wherein the longitudinal direction of the heat sensor corresponds to a longitudinal direction of the anatomical vessel when the heat sensor is deployed in the anatomical vessel.

35. The heat sensing system of claim 30, wherein the encapsulation is configured to transition between the compressed state in which the encapsulation has a first cross-sectional profile and the expanded state in which the encapsulation has a second cross-sectional profile that is larger than the first cross-sectional profile, the encapsulation defining the lateral perimeter of the heat sensor, wherein the lateral perimeter is the same whether the encapsulation is in the compressed state or in the expanded state.

36. The heat sensing system of claim 30, wherein the controller is further configured to activate an alarm when a temperature is detected by the controller that reaches or exceeds a threshold value, wherein a change in the temperature is related to the overall electrical resistance of the heat sensing wire.

37. The heat sensing system of claim 30, wherein the controller is further configured to determine a rate of change of a temperature profile that is monitored by the controller, wherein the rate of change is determined by measuring the changes to the overall electrical resistance of the heat sensing wire over time.

* * * * *

UNITED STATES PATENT AND TRADEMARK OFFICE
CERTIFICATE OF CORRECTION

PATENT NO. : 10,182,725 B2
APPLICATION NO. : 13/763696
DATED : January 22, 2019
INVENTOR(S) : Bunch et al.

Page 1 of 1

It is certified that error appears in the above-identified patent and that said Letters Patent is hereby corrected as shown below:

In the Claims

Column 30, Line 42 reads, "larder than the first cross-sectional profile . . ." which should read, "larger than the first cross-sectional profile . . ."

Signed and Sealed this
Twenty-sixth Day of March, 2019

Andrei Iancu
*Director of the United States Patent and Trademark Office*